United States Patent [19]
Fukui et al.

[11] Patent Number: 5,506,938
[45] Date of Patent: *Apr. 9, 1996

[54] EXPERT SYSTEM DEVELOPMENT SUPPORT SYSTEM AND EXPERT SYSTEM ENVIRONMENT UTILIZING A FRAME PROCESSING TECHNIQUE

[75] Inventors: Chihiro Fukui; Dai Watanabe; Hiroyuki Kudo, all of Hitachi, Japan; Masahiko Amano, Santa Clara, Calif.; Yasushi Harada, Hitachi, Japan

[73] Assignee: Hitachi, Ltd., Tokyo, Japan

[ * ] Notice: The portion of the term of this patent shall not extend beyond the expiration date of Pat. No. 5,228,117.

[21] Appl. No.: 223,404

[22] Filed: Apr. 4, 1994

Related U.S. Application Data

[63] Continuation of Ser. No. 18,581, Feb. 17, 1993, Pat. No. 5,359,701, which is a continuation of Ser. No. 684,662, Apr. 12, 1991, Pat. No. 5,228,117.

[30] Foreign Application Priority Data

Apr. 12, 1990 [JP] Japan ...................................... 2-96924

[51] Int. Cl.[6] .................................................. G06F 15/18
[52] U.S. Cl. .................................................. 395/62
[58] Field of Search ................................... 395/62

[56] References Cited

U.S. PATENT DOCUMENTS 4,967,371 10/1990 Muranaga et al. ...................... 364/513

OTHER PUBLICATIONS

Intelli Corp, Inc., "Model–Based Reasoning in the KEE and Simkit Systems," Intelli News, vol. 2(2), Aug. 1986.

Stelzner, et al; "The Simkit System: Knowledge–Based Simulation and Modeling Tools in KEE," Intelli Corp, Inc., 1987.

Charniak, et al; Artificial Intelligence Programming, 2nd ed., Lawrence Erlbaum Assoc., Pub., 1987, Chapt. 13.

Hu, D., Programmer's Reference Guide to Expert Systems, Howard W. Sams & Co., 1987, 123–141.

Foo, et al., "Databases and Cell–Selection Algorithms for VLSI Cell Libraries," Computer, Feb. 1990, 18–30.

Primary Examiner—Robert W. Downs
Attorney, Agent, or Firm—Kenyon & Kenyon

[57] ABSTRACT

An expert system in which a plurality of knowledge descriptive layers are provided in a frame system. Each descriptive layer is composed of several frames. The frames of the lower knowledge descriptive layer correspond to the elements of a knowledge processing object system. The content of frames of the upper knowledge descriptive layers is determined as an inference made with reference to the frames of the lower layer. This determination is initiated and executed when the content of slots of the frames is updated.

2 Claims, 28 Drawing Sheets

```
( fr1
    super-class    system

S11  10    (when changed    func1(@S11))

S12  5     (when asked      func2(@S12))

method func3( )
    {    ¦
    }    ¦ method end
)
```

FIG. 5

```
( Rule 1                              ( Rule 2
   if                                    if
      ( ?FR1                                ( ?FR1
         @ class = c1                          @ class = c1
         @ limit = 10                          @ limit = 10
         @ value → ?v  )                       @ value → ?v  )
      ( ?FR2                                ( ?FR2
         @ class = c2                          @ class = c2
         @ limit = 20                          @ limit = 20
         @ value > ?v  )                       @ value ≤ ?v  )
   then                                  then
         ( · · ·                               ( · · · ·
)                                     )

( f11                                 ( f21
      class  c1                             class  c2
      limit  10                             limit  20
      value  15                             value  30
   )                                     )
   ( f12                                 ( f22
      class  c1                             class  c2
      limit  10                             limit  20
      value   0                             value  10
   )                                     )
   ( f13                                 ( f23
      class  c1                             class  c2
      limit  20                             limit  20
      value  15                             value   5
   )                                     )
   ( f14                                 ( f24
      class  c1                             class  c2
      limit  15                             limit   5
      value   5                             value  10
   )                                     )
```

FIG. 7

(f12
   class  c1
   limit  10
   value  0
) ⇒

(f23
   class c2
   limit 20
   value  5
) ⇒

(f24
   class c2
   limit  5
   value 10
) ⇒

(f12
   class  c1
   limit  5
   value 100
)

(f23
   class c2
   limit  6
   value 100
)

(f24
   class c2
   limit 20
   value 10
)

Rule 1 SATISFIED    Rule 2 SATISFIED ( S   class   POWER SUPPLY
    VOLTAGE   PRESENT
    SUPPLY     {Sw}
)

( Sw   class   SWITCH
    VOLTAGE   PRESENT
    SUPPLY     {$D_1$, $D_2$}
)

( $D_1$   class   INSTRUMENT
    VOLTAGE   PRESENT
    SUPPLY     {$D_2$}
)

( $D_2$   class   INSTRUMENT
    VOLTAGE   PRESENT
    SUPPLY     { }
)

( $D_3$   class   INSTRUMENT
    VOLTAGE   PRESENT
    SUPPLY     { }
)

FIG. 10
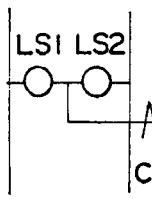 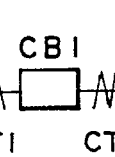 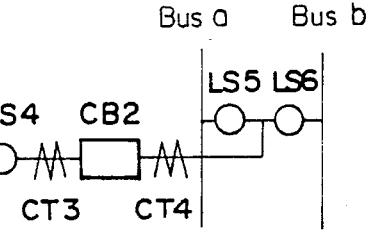 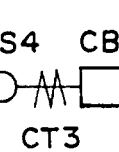
(a)
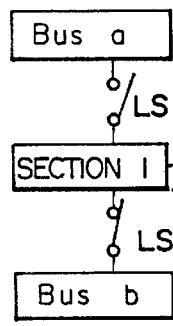 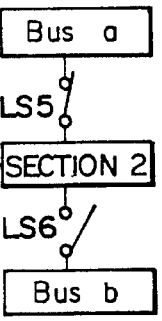
(b)
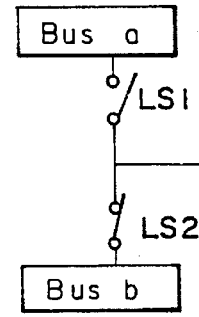 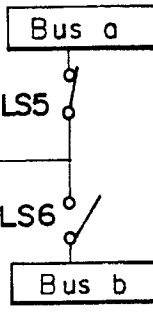
(c)
(d)

1101 SLOT NAME TABLE
1102 SLOT VALUE EVALUATION METHOD TABLE
1103 SLOT VALUE TABLE
1104 FRAME SET DATA

INDEXING DEVICE
23

```
(B₀
    TYPE                        BUS
    LOAD-SIDE
    INSTRUMENTS                 {1Tr, 2Tr, 3Tr}
)
(B₁
    TYPE                        BUS
    POWER-SOURCE-
    SIDE INSTRUMENTS            {1Tr}
    LOAD-SIDE
    INSTRUMENTS                 {F₁}
    CONNECT                     {B₂}
    INTERCONNECTION             {L₁}
)
(1Tr
    TYPE                        TRANSFORMER
    POWER-SOURCE-
    SIDE INSTRUMENTS            B₀
    LOAD-SIDE
    INSTRUMENTS                 B₁
)
(L₁
    TYPE                        TRANSMISSION LINE
    CONNECT                     {B₁}
)
(F₁
    TYPE                        LOAD
    POWER-SOURCE-
    SIDE INSTRUMENS             B₁
)
```

```
(? bus
    TYPE    = BUS      ~2301
    CONNECT ≠ { }
)
```

```
(1Tr
    ◎ TYPE        = TRANSFORMER
    ◎ POWER-SOURCE-    →?b₁
      SIDE INSTRUMENTS
    ◎ LOAD-SIDE         →?b₂
      INSTRUMENTS
)
(?Tr
    ◎ TYPE        = TRANSFORMER
    ◎ POWER-SOURCE-    = ?b₁
      SIDE INSTRUMENTS
    ◎ LOAD-SIDE         = ?b₂
      INSTRUMENTS
        ?Tr                 ≠ 1Tr
)
```

FIG. 30
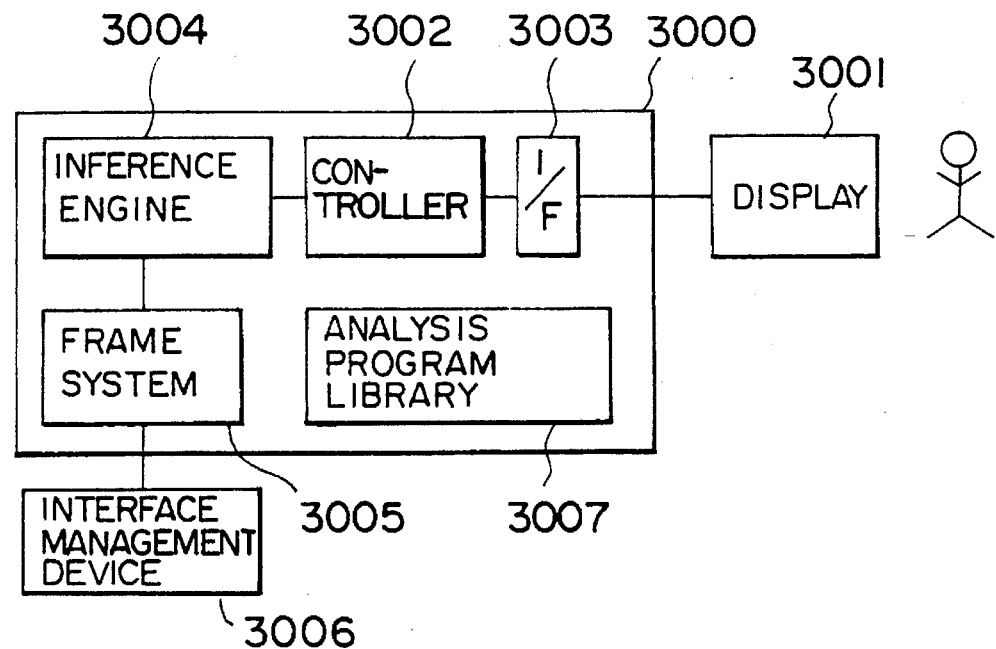
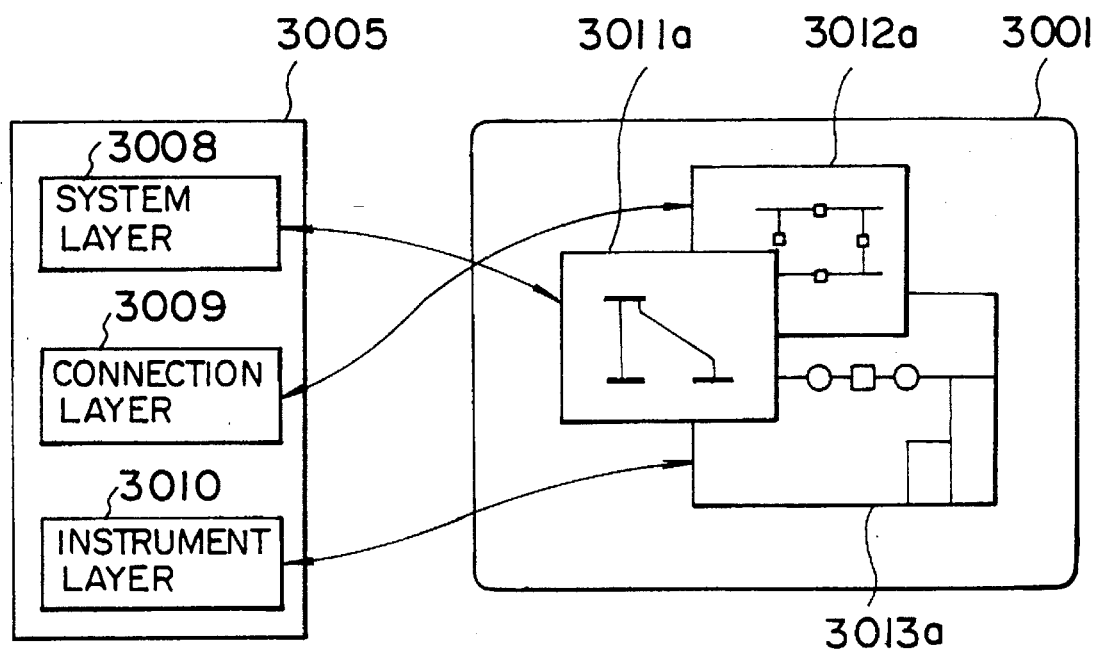

EXPERT SYSTEM DEVELOPMENT SUPPORT SYSTEM AND EXPERT SYSTEM ENVIRONMENT UTILIZING A FRAME PROCESSING TECHNIQUE

This is a continuation of U.S. patent application Ser. No. 08/018,581 filed on Feb. 17, 1993, now U.S. Pat. No. 5,359,701 issued on Oct. 25, 1994, which is a continuation of U.S. patent application Ser. No. 07/684,662 filed on Apr. 12, 1991, now U.S. Pat. No. 5,228,117 issued on Jul. 13, 1993.

BACKGROUND OF THE INVENTION

This invention relates generally to expert systems, and more particularly to an expert system for processing knowledge concerning a large-scale artificial system.

Various systems have been proposed for expert systems that store knowledge of human experts in a knowledge base and make judgments similar to those of the human experts. Currently, the most popular inference method is a so-called production system. Other methods use frames to represent knowledge.

In some of these production systems, the method used is to perform forward reasoning, while in other production systems, the method used is to perform backward reasoning. The production system for performing forward reasoning is a system in which the cycle of recognition and action of a human is modeled. Namely, this kind of production system recognizes the current status and then determines the content of the next action.

FIG. 2 of the accompanying drawings shows the general structure of this production system. As shown in FIG. 2, the production system generally comprises a knowledge base 201 and an inference engine 202. Inside the knowledge base 201 there are included a plurality of rules 203, a plurality of knowledge representations, e.g. a plurality of frames 204, and a work area 205.

The rules 203 include a condition section, which contains condition instructions for recognizing the status stored in the frames 204 or the work area 205, and an instruction section in which the action to be executed is described. Using these rules, the inference engine 202 repeats three steps to execute an inference, i.e. matching process 206, conflict resolution 207 and action 208.

The matching process 206 in the inference engine 202 is the step of retrieving the rules that have condition instructions which match the current status stored in the work area 203 or the frames 205 and then integrating a set of both the matching rules and the status values as a conflict set 209. The conflict resolution 207 is the step of selecting one rule to be executed from the obtained conflict set 209. The action 208 is the step of executing, such as the updating of the content of the work area or the frames, according to the description in the instruction section of the selected rule.

The frames representing knowledge are frames for systematically and hierarchically representing information concerning a knowledge processing object. FIG. 3 shows an example in which knowledge concerning components of an electric circuit is hierarchically represented by frames.

In FIG. 3, a frame 301 of the uppermost class defines an attribute of class as electrical components. In the illustrated example, the frame of electrical components, which define the class of electrical components, has two slots, i.e., name of manufacturing company 302 and date of production 303. Lower frames 304, 305, 306 preceding frame 301 define classes of more specific types of entries, such as resistor 304, coil 305 and condenser 306.

The frame of resistor 304, which defines the class of resistor, has the type of resistor 307 as a slot for storing the type of resistor and has the resistance 308 as a slot for storing the resistance of the resistor.

Thus frames 309, 310 represent knowledge about individual components as follows:

Component R1 of the frame 309 has resistor as class, and hence has type of resistor and resistance, which are slots defined in class of resistor.

The class of resistor 304 of component R1 in the frame 309 is a lower class subordinate to the electrical component 301, and hence succeeds also to the attribute of the electrical component 301, having two slots, i.e. manufacturing company 302 and date of production 303, which are defined in the class of electrical components. Then the actual name of a company and other information are stored in the respective slots to express information about an individual electrical component. The frames are stored in a data base systematically storing data as described above and are capable of storing a process specific to the frames.

FIG. 4 shows an example in which a process specific to the frame is stored by a function called demon and a function called method. In FIG. 4, in the frame fr1, slots S11 and S12 are defined and have stored in them the values 10 and 5, respectively.

In the slot S11, the procedure func1 having a character 'when-changed' is defined as a demon, while in the slot S12, the procedure func2 having a character 'when-asked' is also defined as a demon.

The character 'when-asked' executes when the slot value stored in the slot is referred to externally, while the character 'when-changed' executes when the slot value is updated. Therefore, when the value of the slot S11 is updated, the procedure func1 is executed with the value of the slot S11 as an argument. Also in FIG. 4, func3 is a procedure called method which is a procedure effective only in the frame fr1.

The method func3 is executed by giving the name of method 'func3' as a message passed to the frame fr1 from an external source. After executing the defined processes, the method func3 returns the value of the executed result back as a reply to the frame or rule that sent the message.

As discussed above, a production system is a simple but very general technique. Since frames can systematically represent knowledge, they are widely used in expert systems. However, assuming that the conventional production system and frames are applied to an actual large-scale plant or an artificial large-scale system, such as power, communications or transportation networks, a practical inference speed cannot be achieved.

These problems will now be described item by item in greater detail.

(1) Increase of Time Needed for Condition Judgment called matching process

An inference cycle of the production system is simple and can serve a general purpose. Assuming that this inference cycle is realized progressively on a computer, the amount of computation for condition judgment will increase exponentially as the number of frames is increased.

Accordingly algorithms have hitherto been proposed for increasing the rate of condition judgment of the production system. A typical algorithm is the RETE algorithm. Recently, for example, the TREAT algorithm which is an improvement of the RETE algorithm has been announced.

The RETE algorithm is discussed in Forgy, C. L.: RETE, A Fast Algorithm for the Many Pattern/Many Object Pattern Matching Problem, Artificial Knowledge, Vol. 19, pp 17–37. TREAT algorithm is discussed in Miranker, D. P.: The TREAT, A Better Match Algorithm for AI Production Systems, AAAI-87, pp 42–47. Furthermore, these algorithms are explained in an article in the Journal of the Inference Processing Society of Japan, Vol. 29, No. 5, page 467.

In short, one feature of condition judgment algorithms, including the RETE algorithms, is that the number of condition judgments is reduced by previously analyzing rules to provide a combination of rules having a common condition clause, constituting a data flow graph called 'RETE network' or "rule network" and commonly using the flow graph for computation of the individual condition clause. Another feature of such condition judgment algorithms is that the interim result of conditional judgment is computed by recomputing only the portion influenced by the previous execution step and combining that portion with an interim result unchanged from the previous execution, reserving the interim result of the preceding inference cycle.

The movement of this RETE algorithm will now be described in connection with a simple rule shown in FIG. 5. In FIG. 5, a term with question mark (?) affixed at its head represents a variable, and a term with an at sign (@) affixed at its head represents a value of a designated slot. An arrow (→) indicates the value to be substituted. ?FR1 and ?FR2 in the condition section of the rules are variables representing the names of frames, and ?v is a variable to be substituted by the value of slot 'value'. Therefore, Rule 1 represents the rule: execute the instruction section if there is a frame ?FR1 in which the class is c1, the value of slot 'limit' (slot kind identification No.) is 10 and if there is a frame ?FR2 in which the class is c2, the value of slot 'limit' is 20, and the value of slot 'value' is larger than ?v (i.e., larger than @ value of ?FR1).

Rule 2 represents the rule: execute the instruction section if there is a frame ?FR1 in which the class is c1, the value of slot 'limit' (slot kind identification No.) is 10 and if there is a frame ?FR2 in which the class is c2, the value of slot 'limit' is 20, and the value of slot 'value' is smaller than ?v (i.e., larger than @ value of ?FR1 ). And, there exist frames {f11, f12, f13, f14, f21, f22, f23, f24}. As shown in FIG. 5, {f11, f12, f13, f14} belongs to the class c1, and {f21, f22, f23, f24} belongs to the class c2. FIG. 6 shows the condition section of the rule of FIG. 5 as a rule network.

The RETE algorithm will now be described in connection with FIG. 6. In the rule network, the portion in which the individual condition clause is to be judged is represented by a node.

In FIG. 6, 601 designates a route node serving as an inlet from which a frame, which is to be judged, flows into the rule network; 602, a node at which the judgment is to be made as to whether the class of frame is c1 or not; and 603, a node at which the judgment is to be made as to whether the class of frame is c2 or not. 604 designates a node at which the judgment is to be made as to whether the value of slot 'limit' is 10 or not; and 605, a node at which the judgment is to be made as to whether the value of slot 'limit' is 20 or not. 606 designates a node at which the judgment is to be made as to whether the value of slot 'value' of ?FR1 is smaller than the value of slot 'value' of ?FR2; and 607, a node at which the judgment is to be made as to whether the value of slot 'value' of ?FR1 is larger than or equal to the value of slot 'value' of ?FR2. The nodes 602 through 605 are called "intranodes", while the nodes 606 and 607 are called "internodes".

A set of frames {f11, f12, f13, f14, f21, f22, f23, f24} to be judged is let to flow from the route node 601 to the rule network; the frame matched with the condition judgment at each node is stored in that node and is transmitted to the next node via a branch. 608 designates a set of frames matched with the condition judgment of the node 602; 609, a set of frames matched with the condition judgment of the node 603; 610, a set of frames matched with the condition judgment of the node 604; and 611, a set of frames matched with the condition judgment of the node 605.

The internode 606 combines the frames passed from the condition judgment of the intranodes 604 and 605 to judge a set of frames matched with the condition of Rule 1. The arithmetic operation at the node 606 is to obtain a combination of two sets of frames by a JOIN operation, the result of the operation being designated by 612. The first set of frames {f11, f21} 612 shows that f11 match with the frame names ?FR1 of the first condition clause of Rule 1 and f21 match with the frame names ?FR2 of the 2nd condition clause of Rule 1, and that the condition section of Rule 1 is satisfied by the combination of them.

Of a set of frames stored at each node, the frames stored in the intranode are called "α memory", and the frames stored in the internode are called "β memory". Now assume that the slot values of frames f12, 123, 124 are varied as shown in FIG. 7 by adoption of a rule. In this case, in the RETE algorithm, the updated frames are canceled from both α memory and β memory of the rule network, whereupon the further updated frames are let to flow from the route node to the rule network, to be recomputed and to reconstitute the interim memory (α memory and β memory).

FIG. 8 shows the varied interim memory of each node after performing this reconstitution work. Since the amount of computation required for reconstitution of this interim memory is increased in an applied field such that the interim result of the previous cycle is changed markedly by the rule execution, the RETE algorithm cannot adequately be effective in applied fields to increase the rate of condition judgments.

To cancel the updated frames from both α memory and β memory, it must be determined which node the frame is stored in. This can be realized usually by letting the frame, while keeping its previous value, flow in the rule network and by canceling data about the frame from the memory of the reached node. Then the updated value of the frame is allowed to flow through into the network.

In reconstituting the interim memory, as the number of frames that are updated increases, the computation increases. Partly since a practical large-scale plant or an artificial large-scale system, such as electrical power, communications or transportation network, is composed of a great number of components, and since a great number of frames corresponding to every kind of standardized components for each class exist, if components of the same standard are represented in terms of frames, and data of a great number of frames is updated at every inference cycle, it is inevitable that inference time would increase due to the increase in process time for reconstituting interim memory.

To this end, the TREAT algorithm has been proposed. This algorithm does not maintain β memory but maintains only α memory as interim memory so that a dynamic JOIN arithmetic operation is optimized at every inference cycle to improve the rate of memory management. In general, since the status value to be updated is large due to the execution of one rule in an inference in actual time, the TREAT algorithm is known as a high-speed condition judgment algorithm suited to a real-time process.

However, assuming that the TREAT algorithm is adopted in a large-scale artificial system, α memory is managed as interim memory increasing the computation needed to reconstitute this interim memory so that an increase in inference time is still inevitable. Because of the interim memory, these algorithms have many frames and hence are not suitable to a system in which data of a great number of frames needs to be updated.

A large-scale artificial system that has many frames and requires data of a great number of frames to be updated every inference process will now be described referring to a practical inference process. FIG. 9 shows a power supply route to various instruments in an electrical power system. 901 designates a power supply source; 902, a switch; and 903, 904 and 905 designate instruments which receive the power supply. One instrument 904 receives power via another instrument 903. For each instrument, it is necessary to define frames as shown in FIG. 9, increasing the number of the frames. In each frame, the slot named 'voltage' represents the status of whether or not the instrument is receiving power. The slot named 'supply' represents a set of instruments to which power is supplied from the instrument.

In this case, the inference process to discriminate as to which instrument happens to shut down when the switch 902 becomes out of order will now be considered. To realize such an inference process by rules, the rule to make a judgment of power failure will be such as "If the value of slot 'voltage' is 'Nil' and if the value of slot 'voltage' of the frame stored in slot 'supply' is 'present', substitute 'Nil' for slot 'voltage' of the frame."

The above-mentioned method can also be used, in this case, assuming that a demon having a character called 'when-changed' is defined for slot 'voltage' and that the value 'Nil' is substituted for slot 'voltage', a message to request substitution of the value 'Nil' for slot 'voltage' in every frame stored in slot 'supply' is transmitted. Thus in the process of inference, 'voltage' slots of many frames are successively updated.

The inference process for judgment of power failure is to recognize the status of an object system given less information and knowledge concerning the constitution of the object system. As mentioned above, in a large-scale artificial system, there are many frames, and data of a great number of frames are updated by individual inference processes.

(2) Increase of Time Needed for State Recognition

In an expert system to be applied to an actual artificial system, there is a step to grasp the status of the actual artificial system, irrespective of its purpose. In a practical system, its status varies constantly; updating of knowledge resulting from such fluctuation is inevitable when performing a proper inference.

In a conventional expert system, if an inference is started externally by an instruction or the like, an inference engine first fetches the external status values and then makes a discrimination on the situation by using such external data, whereupon an inference for the original purpose is carried out. Otherwise, when it becomes necessary to grasp the situation during inference execution, the external status values are retrieved and recognized.

According to technology disclosed in, for example, "Expert System for Discrimination of Failure Section Based on Generalized Rules", Institute of Electrical Engineers of Japan 1988, PE-88-26, during executing an inference of a failure section in an electrical power system, the status of each relay is examined to determine the status of the previous step, and the section of protection of each relay is determined and recognized by inference.

Therefore, in a large-scale system in which there exist many situations to be grasped, discriminating the situation would take an unallowably long time.

3) High Load of Inference Engine due to Complexity of Knowledge according to Combined View Point In an expert system to be applied to an actual large-scale system, as the purpose for inference becomes complex, like knowledge expressions are not always used even for the similar object system, thus requiring various knowledge expressions. This problem will now be described in connection with FIG. 10.

FIG. 10(a) is a block diagram (systematic diagram) showing an electric power system which comprises a substation A, a substation B and a power-transmission line C connecting the substations A and B. There are a pair of buses a and b in each substation A and B. Between each pair of buses a and b and the power transmission line C, there are located switches LS1–LS4 and breakers CB1–CB2, along with current transformers CT1–CT4 used as current measuring instruments.

To make an inference for a discrimination of failure in this system, the individual instruments need to be represented as frames corresponding to the arrangement shown in FIG. 10(b). To make an inference for making a system operation plan for changing the connection status of the instruments in this system, no measuring instrument is necessary so that the individual instruments need to be represented as frames corresponding to the arrangement shown in FIG. 10(c). To make a calculation of power flow, i.e., to calculate distribution of electrical energy, only knowledge about the buses as nodes and about the power transmission line is needed as shown in FIG. 10(d).

In the foregoing examples, the knowledge representing methods were suitable for various purposes. In an actual expert system, it is usual that these purposes would come up in combination. If knowledge representation and instance frames were therefore defined for every purpose, the larger the system, the larger the number of frames thus increasing the computation for condition judgment steps of a production system, and resulting in an increased inference time. In the meantime, if various purposes were accomplished by a small number of instance frames, rules become complex and increased in number thus increasing the number of inference steps to be made until the purpose is achieved.

As discussed above, in an expert system to be applied to an actual large-scale system, the inference engine would undertake a high load due to the complicated knowledge, thus increasing the inference time. In a practical system, object data is updated frequently like the status of the switches LS1, LS2, etc. of FIG. 10. In this case, it is necessary not only to update the slot value storing the updated status value, but also to update all the associated status values so as not to cause any contradiction. This is a significant problem particularly in an expert system adopting a real-time process. In a production system, however, no adequate method for solving this problem is known. Thus the conventional production system would encounter an increase of inference time when applied to an actual large-scale system.

In a public system such as an electric power system or a communication system, an increase of inference time means an increase in recovery time when a fault occurs, which is a serious problem.

SUMMARY OF THE INVENTION

It is therefore an object of this invention to provide an expert system which enables a high-speed inference by reducing the load on an inference engine in an expert system even when applied to a large-scale system.

According to a first aspect of the invention, there is provided an expert system processing knowledge of an object system, including a knowledge base comprising: a unit knowledge element descriptive layer including a collection of unit knowledge elements in each of which knowledge of an element of the object system is described; and one or more summarized knowledge element descriptive layers arranged above the unit knowledge element descriptive layer as an upper layer or layers and each including a collection of summarized knowledge elements in each of which the knowledge in the respective lower layer is reconstituted in abstracted or summarized form.

Thus the knowledge about a knowledge processing object system is provided in abstracted or summarized description according to the processing purpose, presenting an easy to use knowledge base. Furthermore, the layer to which a knowledge element attributes may be either visible or latent to a user of the knowledge base. If visible, it is possible to provide knowledge layer by layer, thus making the use of knowledge of the knowledge base much more convenient.

Since the knowledge in summarized knowledge elements of the knowledge base can be used, only simple inference rules to be executed by an inference engine in the expert system are required, thus realizing a high-speed inference.

According to a second aspect of the invention, there is provided an expert system, comprising:

(a) a knowledge base for storing knowledge expressed by frames each having one or more slots in each of which a knowledge is described as a slot value; and (b) an indexing device including
  (i) a managing device for managing the frames according to kinds of slots in the frames in terms of the slot values,
  (ii) a reorganizing device reorganizing the content of management of the managing device, according to the updated content of the slot value, as a background process updating the slot value, and
  (iii) a retrieving device for retrieving, from a designated slot kind and a designated information concerning slot value, a set of frames in which the slot value related to the designated information is stored in the designated kind of slot. Because of these devices, it is easy to make an inference in terms of slots.

Since the previous reorganizing device reorganizes the content of management of the managing device, according to the updated content, as a background process to be started by updating the slot values, high-speed inference can be executed.

BRIEF DESCRIPTION OF THE DRAWINGS

FIG. 5 shows typical rules and frames.

FIG. 7 shows changes of frames due to the execution of rules.

FIG. 10(a) through 10(d) shows various knowledge representations corresponding to inference purposes in an electric power system.

FIG. 21 shows the structures of frames representing instruments constituting a system for which a power flow computing process is to be performed.

FIG. 30 is a block diagram showing an interactive electric power system analysis system and a typical display screen according to a fifth embodiment of the present invention.

DETAILED DESCRIPTION

Figure 1:
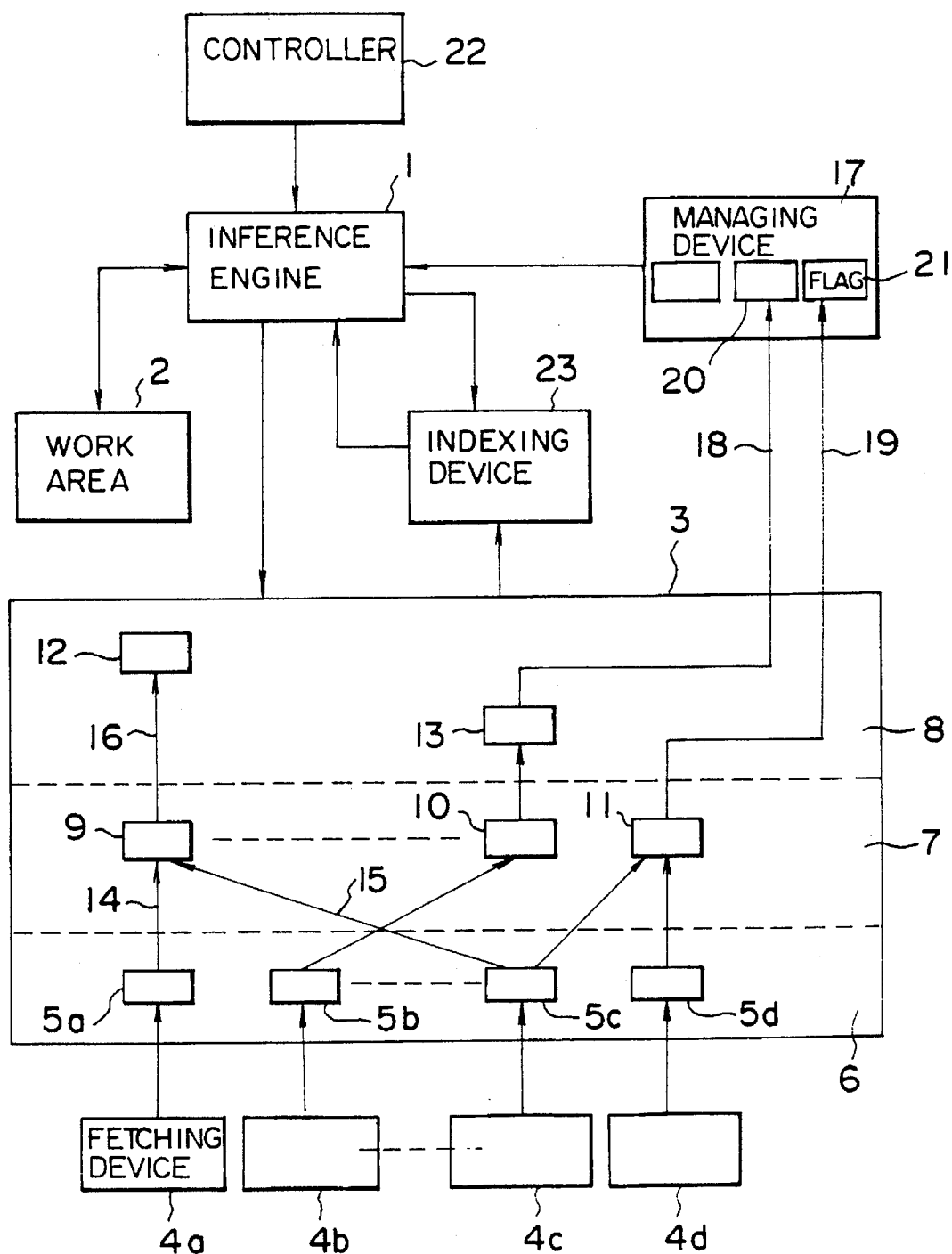
FIG. 1 is a block diagram showing an expert system according to a first embodiment of the present invention.
Figure 2:
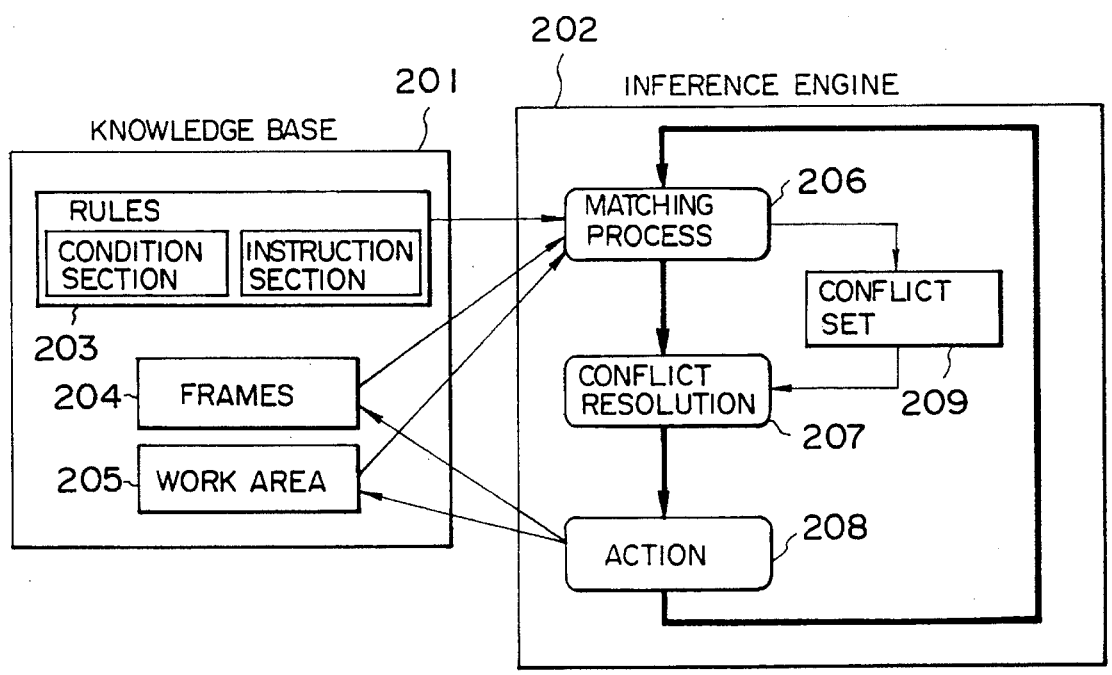
FIG. 2 is a block diagram showing a conventional expert system.
Figure 3:
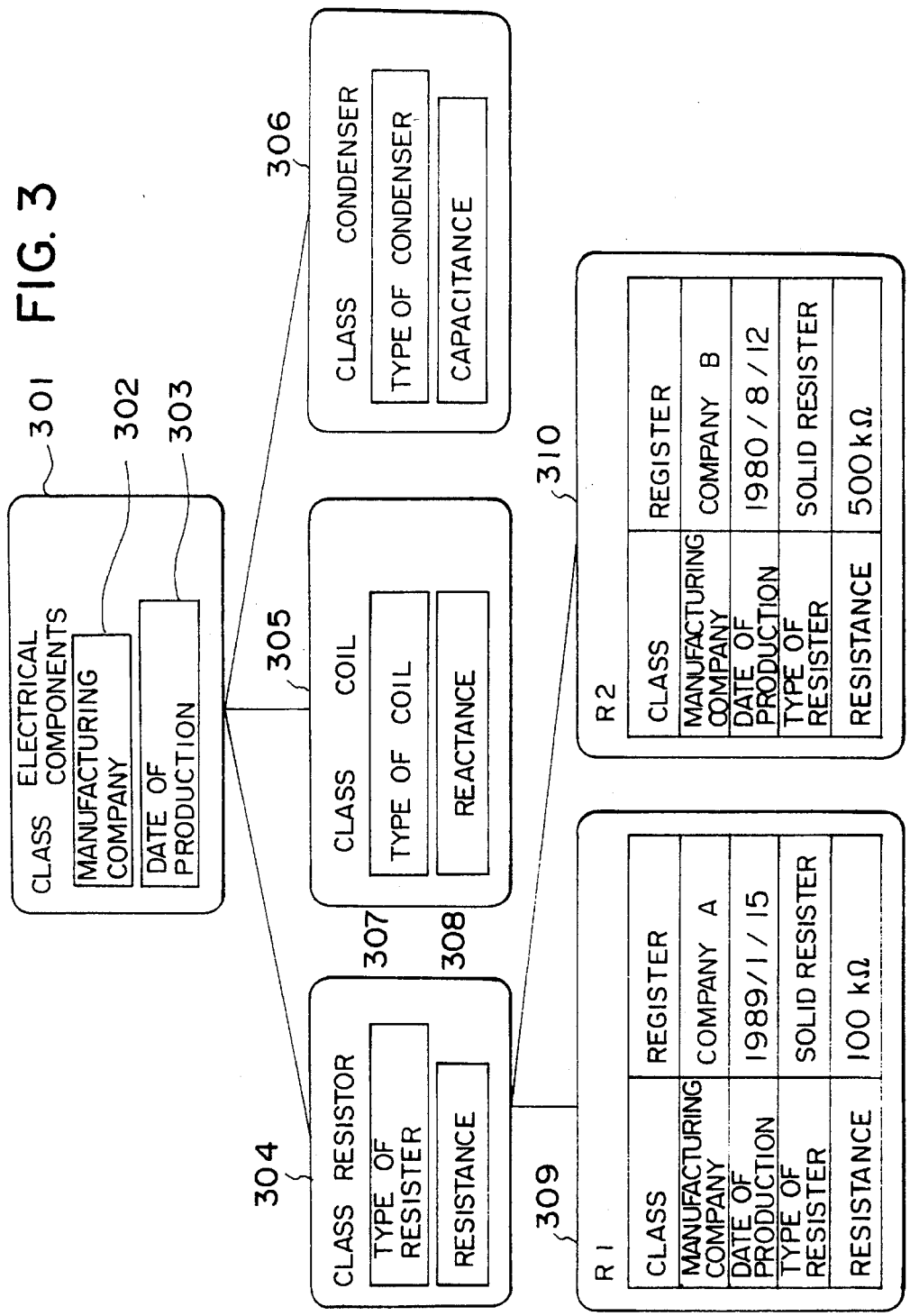
FIG. 3 is a diagram showing the structure of frames.
Figure 4:
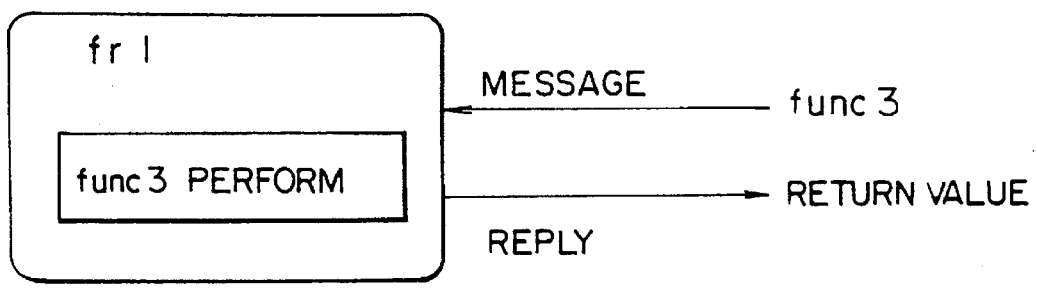
FIG. 4 shows a typical method and a typical slot which are defined in a frame.
Figure 6:
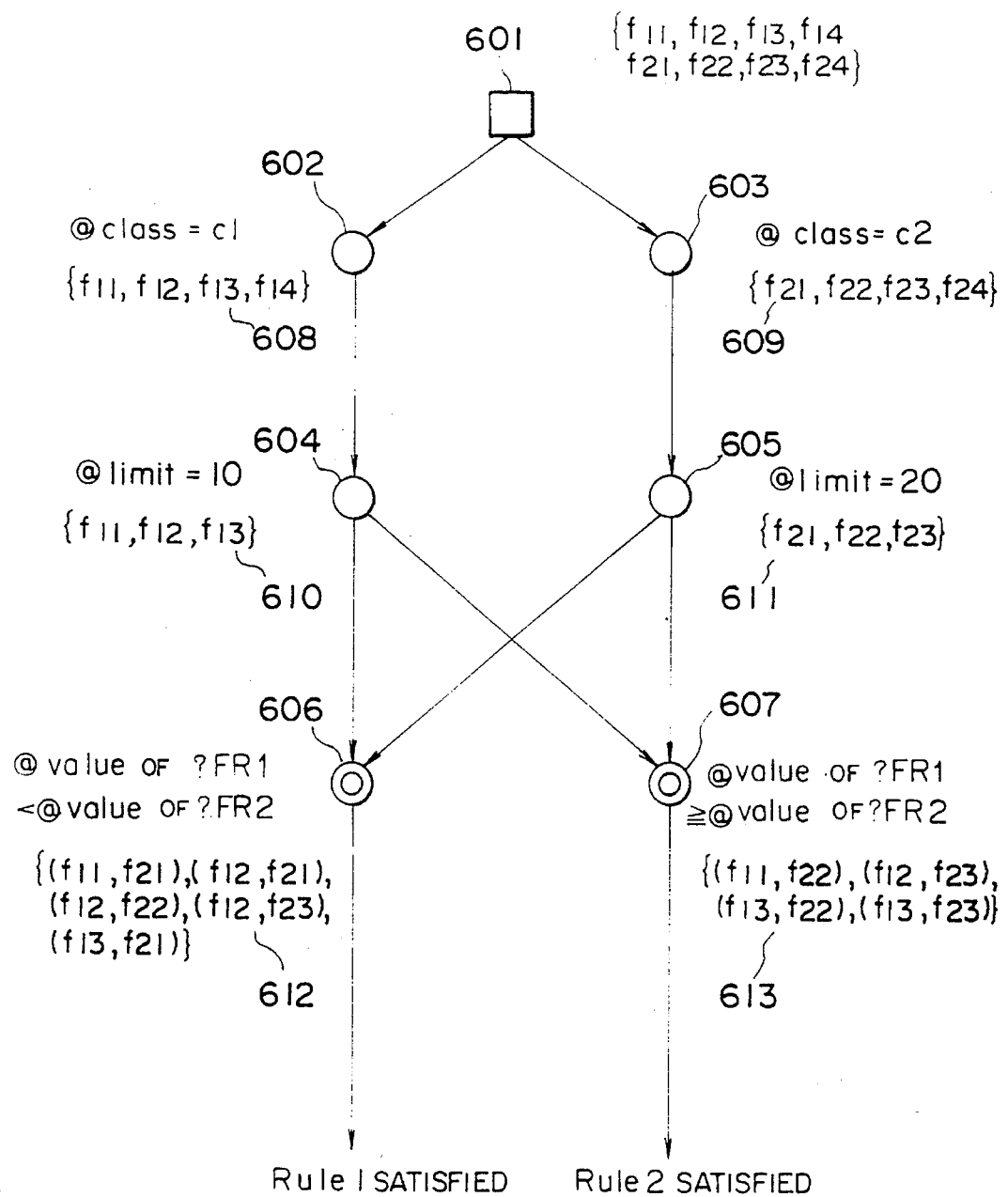
FIG. 6 is a diagram showing the structure of a rule network according to the RETE algorithm.
Figure 8:
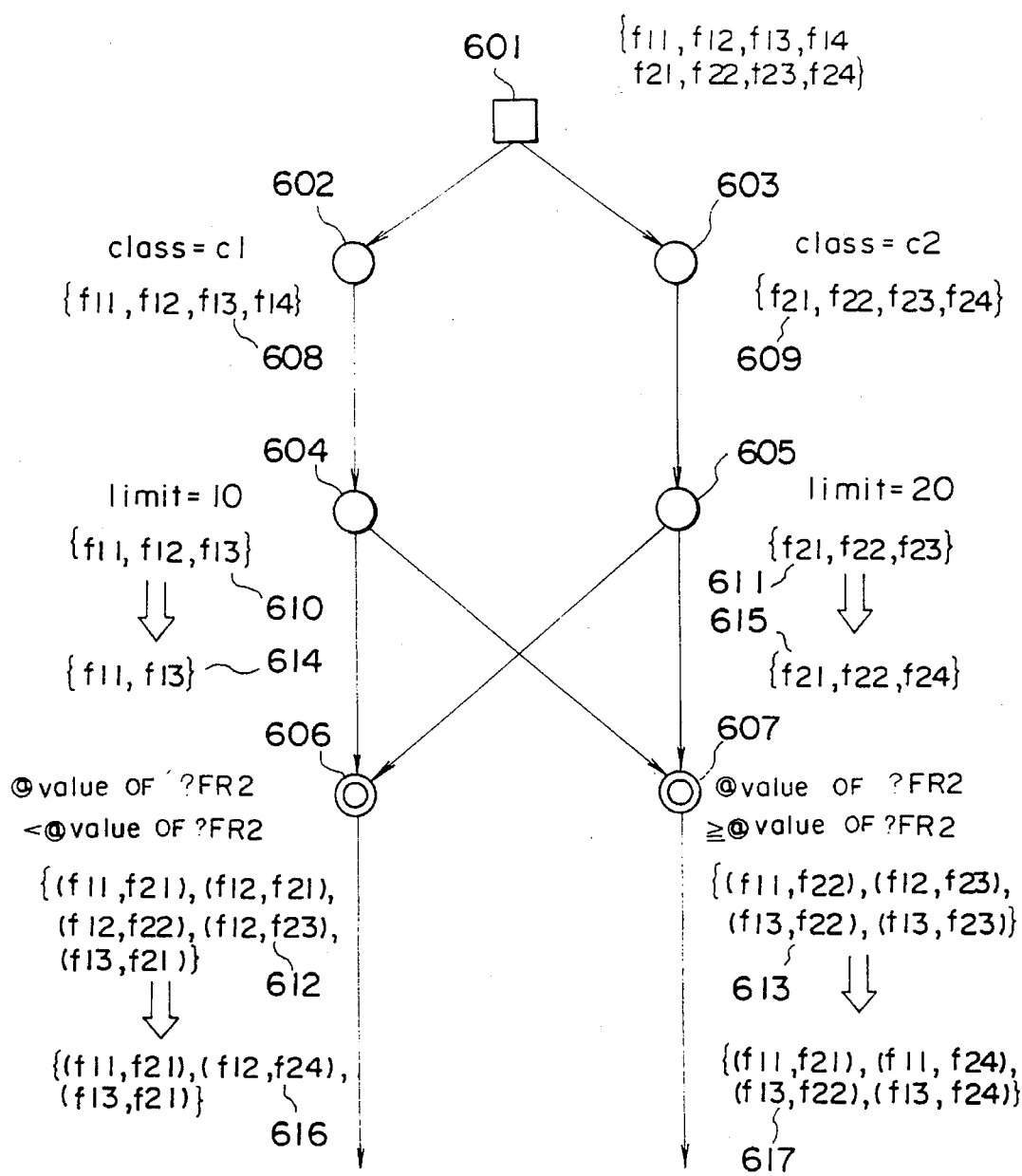
FIG. 8 is a diagram of a rule network illustrating changes of interim memory due to the execution of rules.
Figure 9:
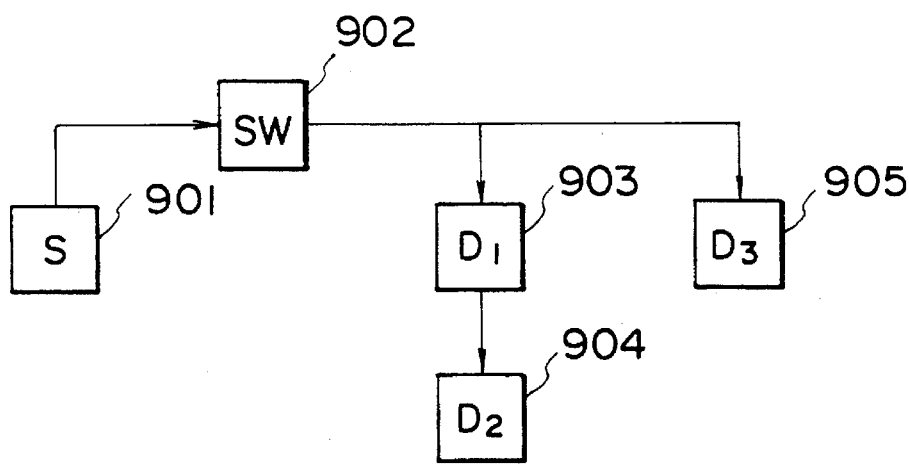
FIG. 9 shows a typical influence of the changes of frames.

The principles of this invention are particularly useful when embodied in an expert system in which knowledge is represented in frames. First of all, a knowledge processing method in the expert system will be described. The knowledge processing method has three primary features itemized as follows:

(1) The system is equipped with two operating modes, i.e. a foreground process and a background process. Here in this specification, the term "background process" means an event-starting-type inference process to be executed when the slot values of frames are updated by, for example, the change of an external event and an explicit instruction. The term "foreground process" means an instruction-starting-type inference process to be executed by a request since an explicit purpose is given.

In this embodiment, the load of an inference engine during the inference is reduced by executing the inference for situation judgment when the status value of the external is changed, thus allowing a high-speed inference. In the process of inference by the background process, when a judgment is made that an event occurred, it is possible to start the foreground process because this event is a trigger.

(2) A frame indexing device is provided in a knowledge base. Regarding a set of frames in which slots having the same identification name, the indexing device stores the frames in terms of slot values.

The inference engine is equipped with a condition judging device for computing, in the judgment of condition step, the judgment of individual condition clauses of a condition section of rules as an inquiry to the indexing device. In other words, a condition judgment is made not by a rule network holding an interim memory. Rather, such judgment is made by using the indexing device, which can be reconstituted easily, because the frames are arranged in order for every kind of slots. Furthermore, since the adjustment and storage of individual frames are previously updated by the background process when the status of the individual frames are changed, it is possible to make a condition judgment at a high speed during the practical inference.

This constitution is particularly effective in a large system in which the slot values stored in particular slots of frames representing constituent elements of the system are discrete and in which the number of kinds of the slot values is relatively small.

For example, according to the disclosure in "Expert System for Discrimination of Failure Section Based on Generalized Rules", Institute of Electrical Engineers of Japan 1988, PE-88-26, relays inoperative during inference of a failure section are recognized one by one by condition judgment. In the indexing device of this embodiment, partly since slots showing operative/inoperative are provided in instance frames corresponding to the individual relays, and partly since the individual frames are managed such as in terms of slot values, it is unnecessary that the inference engine should make such condition judgment for every slot value.

(3) In a frame system, one or more summarized knowledge element descriptive layers each composed of a set of frames storing data of the summarized knowledge element in which knowledge of a lower layer is reconstituted in summarized or abstracted form according to purpose, are arranged hierarchically in order. The lowermost layer is a unit knowledge element descriptive layer including a set of instance frames storing data of elements constituting an object to which the expert system is applied.

The frames of the summarized knowledge element descriptive layer are defined according to the view points of what purpose the frames are used for. Generally, in an expert system for a special purpose, the summarized or abstracted knowledge expressions used in an inference are limited. For this purpose, previously in a background process, knowledge can be summarized or abstracted. And in a predetermined regular process, it is possible to perform summarized or abstracted work speedily without making any inference.

The lowermost layer stores unit knowledge elements storing data corresponding to the real status value of an object system to which the expert system is to be applied. An upper layer above this layer represents abstract status values derived successively from knowledge of the unit knowledge element layer. Thus knowledge corresponding to levels of various view points in various inference processes are stored hierarchically; thereby it is always possible to reduce the load of an inference engine, realizing an increased the rate of inference.

Furthermore, by dividing the frames into layers, the rules of the inference engine can localize the frames to be an object of condition judgment. Namely since the rules can designate the area to be judged by layer, it is possible to further reduce the load of the inference engine. Furthermore, for example, updating the frames of this summarized knowledge element descriptive layer is performed in the background mode. An expert system according to a first embodiment of this invention will now be described. In FIG. 1, reference numeral 1 designates an inference engine, which can usually be realized by a computer; 2, a work area; and 3, a frame system having a hierarchical structure. 4a through 4d designate a device for fetching information concerning external instruments that constitute an object system; 5a through 5d, designate instance frames, which represent the knowledge of these external instruments; and 6 designates a knowledge descriptive layer, which is the lowest layer in the frame system 3. The frame system 3 can be an expert system development support system such as a domain shell. Each frame provided by the frame system is stored as a knowledge base in a storage of a computer. 7 and 8 designate a knowledge descriptive layer which is defined above the lowest layer 6 and which stores the summarized knowledge of the status values of the lowest layer 6.

In FIG. 1, there are shown only two layers 7 and 8. The number of layers should by no means be limited to this specific example. 9 through 13 designate frames defined in the upper layers. Arrows between frames described in the frame system 3 indicate the inference process for determining the status value of a frame in the upper layer with reference to the status of a frame in the lower layer. For example, the arrows 14 and 15 indicate that the status value of the frame 9 is determined from the status of the frames 5a and 5c, respectively. 16 indicates that the status of the frame 12 is determined from the status of the frame 9.

The inference process indicated by these arrows can be executed as a result of condition judgment of the condition section of rules in the foreground process, and can be otherwise executed by a method that is started from a demon by the change of slot values in the background process. 17 designates a device for managing the status of the system and for storing information that represents that an event occurred when a frame in the frame system 3 assumed a particular status. The arrows 18 and 19 indicate the manner in which the event occurred; when the frame 13 assumed a designated status, a flag 20 representing the event is stored in the managing device 17 by the process 18. And a flag 21 is stored in the managing device 17 due to the change of the frame 11 by the process 19.

The inference to be performed in the foreground mode by the inference engine 1 is started by an instruction or the like from a controller 22 for managing an interface with the upper device. This inference can also be started when a particular flag is stored in the managing device 17.

14 through 16 in FIG. 1 indicate an inference in the background mode, specifically illustrating the updating of the summarized frames 9, 10 and 12, which, for example, can be performed by a demon of the updated summarized frame 9 or the instance frame, 5a and 5b updated by the fetching devices 4a and 4b, namely, the updating of data. By realizing the updating work by an object frame system, it is possible to flexibly follow the change of the expert system. Furthermore, the system has excellent expansion and maintenance features.

23 designates an indexer for indexing via slot values. The indexing device 23 is called from the inference engine when the inference engine 1 executes the condition judgment step, and retrieves the frame which satisfies a particular slot condition.

Figures 11, 12:
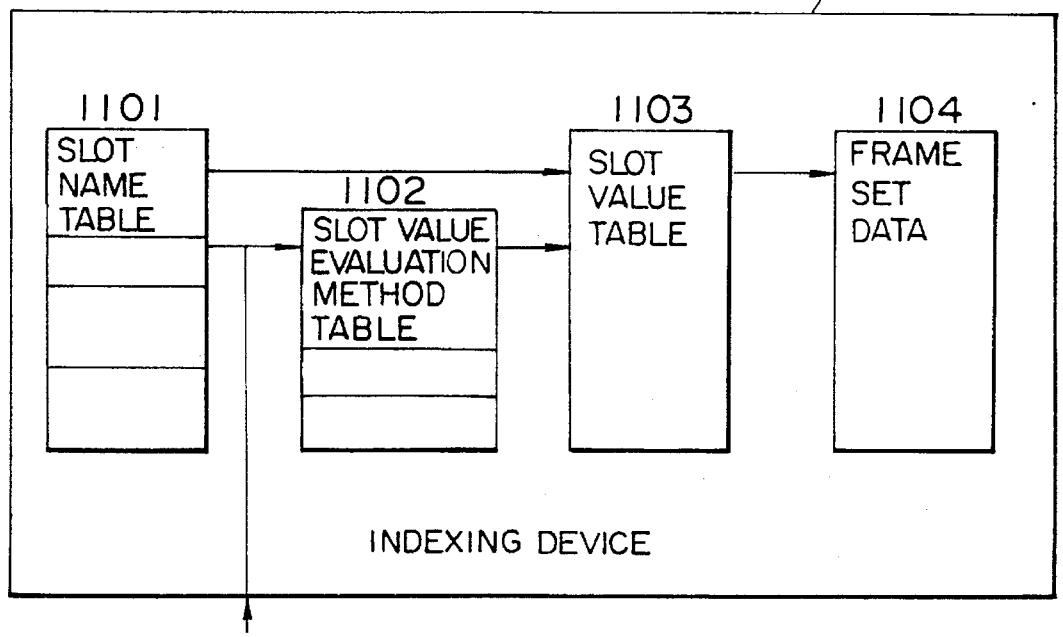
FIG. 11 is a diagram showing the structure of a slot value indexing device.
FIG. 12 shows typical definitions of frames.

Furthermore, even when the slot value of the frame is updated, the indexing device is initiated to update information for indexing. FIG. 11 schematically shows the indexing device 23. As shown in FIG. 11, the indexing device 23 comprises a slot name table 1101, a slot value evaluation method table 1102, a slot value table 1103, and frame set data 1104.

Figure 13:
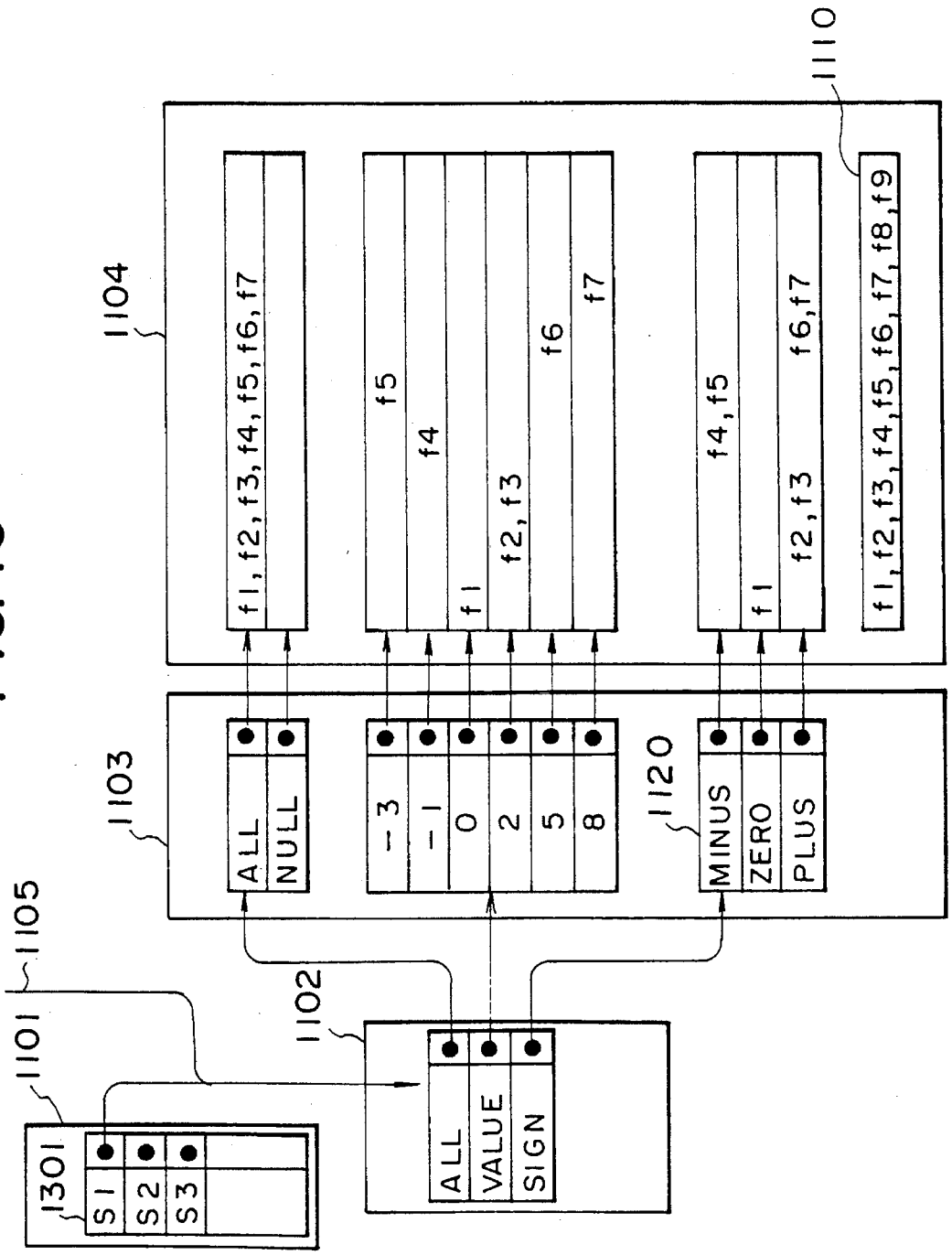
FIG. 13 a diagram showing the detailed structure of the indexing device.

FIG. 12 shows a typical frame, and FIG. 13 shows a portion of the indexing device 23 in connection with the slot, which is an S1 slot (here this slot is called slot S1). The frames which satisfy the condition "S1=2" will now be obtained.

First, a pointer for the slot S1 is retrieved from the slot name table 1101. This pointer designates a table concerning the slot S1 in the slot value evaluation method table 1102. By this and the evaluation of the slot value (here an evaluation device simply determining the slot value) designated by the inference engine, the pointer designating VALUE is selected.

From this pointer, a table of the slot value table 1103, concerning the slot value of the slot S1, can be referred to. Now because what should be located is a frame "S1=2", a key value 2 in the slot value table is located. From the pointer stored concerning the key value 2, it will be noted that the frame to be obtained is the frame set {f2, f3} in the frame set table 1104, since the slot S1 has the value 2 in the frames f2 and f3.

"ALL" in the slot value table means all frames that S1 is defined, and "NULL" means the frames that any slot value is not yet defined. With this structure, it is also possible to retrieve other slot conditions easily.

For example, in the case that a condition is "S1≠2", {f1, f4, f5, f6, f7} can be obtained from the difference between {f2, f3} of "S1=2" and {f1, ... , f7} of ALL. Similarly, the condition "the frame in which S1 is not defined" can be obtained, as {f9, f9}, from the difference between "ALL" and all frame sets 1110.

Furthermore, for example, the condition on plural values of S1 "S1=5 or S1=8" can be obtained by an arithmetic operation such as a logical AND or logical OR of frame sets. In this case, a result of OR operation of the following frame sets:

S1={f6}

S1={f7} corresponding to the respective values is obtained, resulting in {f6, f7}.

If the condition is "S1>0", a set {f2, f3, f6, f7} is obtained by operating OR of S1 2 or 5 or 8. In the case of "the frame having the Maximum value of S1", the maximum value of the slot value table is retrieved. The slot value evaluation method table 1102 will now be described more in detail. In this case where "S1>0", there are very many slots which have values such that S1>0 or in the case that same condition is used repeatedly during the inference, it is desirable to use a different evaluation criteria rather than the simple slot value evaluations on the value of S1.

Consequently, plural slot value tables corresponding to the respective evaluation criteria are required. The slot value evaluation method table 1102 is a table from which a slot value table needed for the retrieving is to be selected. In the case where "S1>0", the frames which satisfy the conditions such as S>0 and S<0 can be retrieved easily by providing the slot value table 1120 corresponding to the sign of value of S1.

As an example in which there are many kinds of evaluation criteria with respect to a single slot value, one case where the slot value is a complex number will now be illustrated. Following are evaluation criteria of complex number a+bi:

| | | |
|---|---|---|
| 1) Value | $(a, b)$ | |
| 2) Actual | $a$ | |
| 3) Image | $b$ | |
| 4) Phase | $\arctan(b/a)$ | |
| 5) Distance | $\sqrt{(a^2 + b^2)}$ | |

Figure 14:
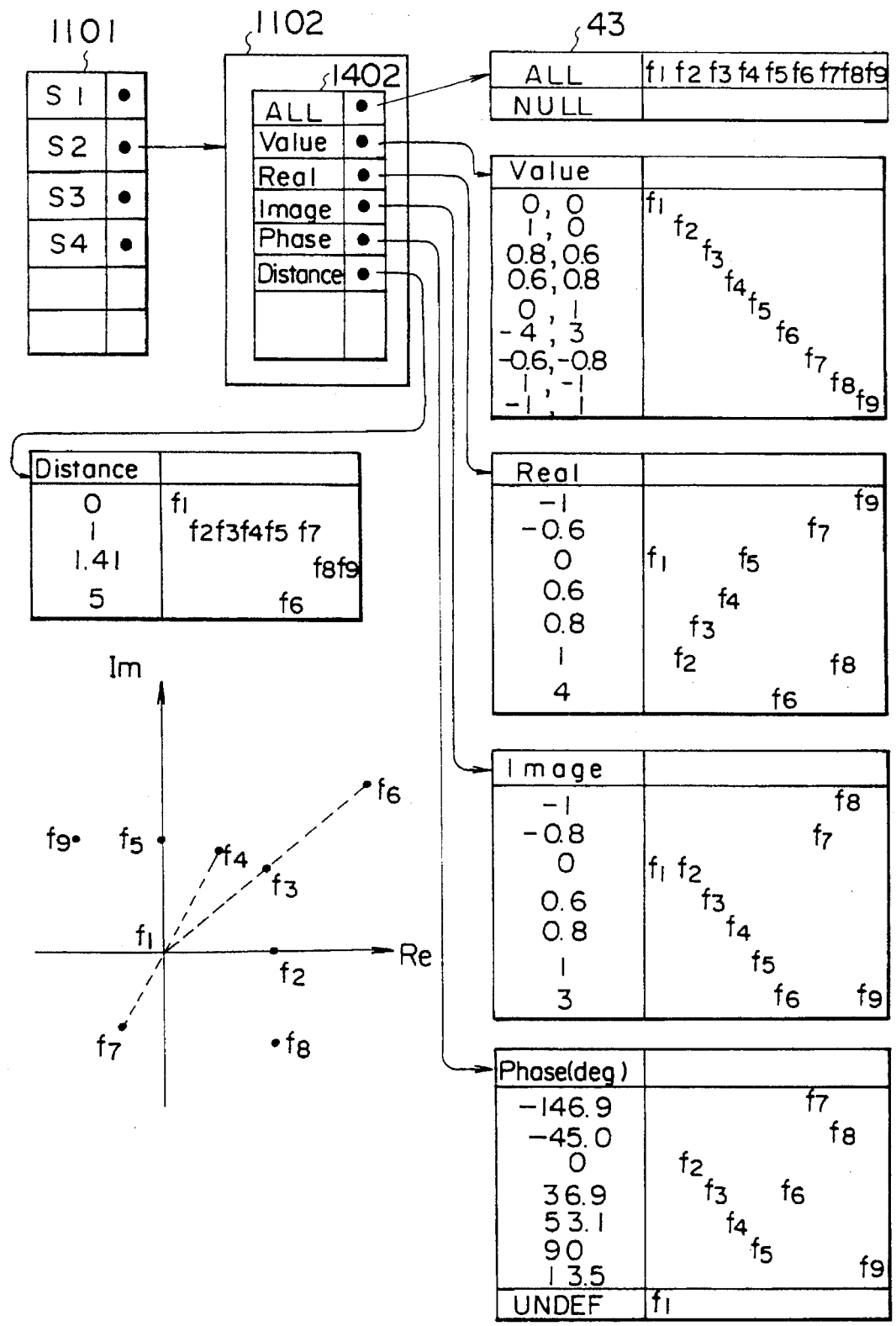
FIG. 14 is a diagram showing the structure of the indexing device having special assessment criteria.

FIG. 14 shows a retrieving device having slot value tables according to all the above-mentioned evaluation criteria for the slot S2 of the frame of FIG. 12. From the slot name table 1101, the slot value evaluation method table 1402 for S2 is retrieved. The set of frames to be obtained can be obtained by the slot value table 43 corresponding to the selected evaluation method. In FIG. 14, the individual slot value tables are redundant. For example, every pattern of the value can be retrieved by the two tables 'Real (Actual)' and 'Image'. If the values of 'value' are previously sorted in terms of actual values, the table 'Actual' can be omitted.

How the slot value evaluation method and the slot value table are constructed is selected by a user or is automatically discriminated by the system, considering both the effect of retrieving and the allowance of a memory. The foregoing way of thinking about a complex number can be expanded to a general vector value.

Figure 15:
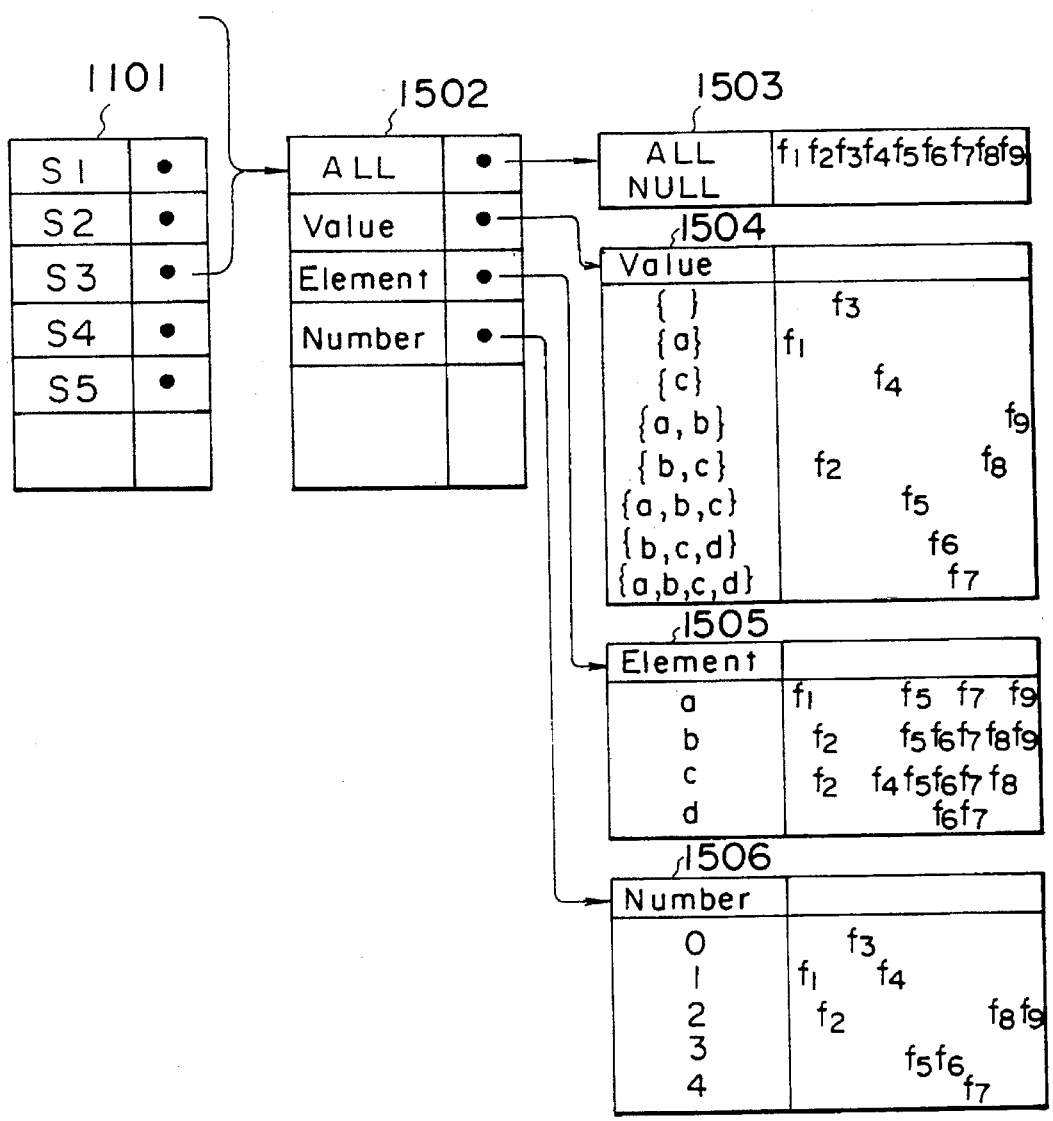
FIG. 15 is a diagram showing the structure of the indexing device in which slot values are represented in terms of sets of elements.

The structure of the indexing device when the slot value is a set will now be described. FIG. 15 shows an indexing device in which S3 is the value of the set. The value of a set can simply be any combination of all elements of the set. The slot value table of frames of FIG. 12 is like the table 1504 in FIG. 15.

If there are a few combinations of this value of set (hereinafter called "combination value"), the table of such combination values is inconsequential. Generally, since there are n combination values for n number of elements, this table technique is not desirable in the case of many elements. In general, it is difficult to set a standard for sorting combination values.

For retrieving a set value, a table Element 1505, in which individual element values are evaluation criteria, and a table Number 1506 in which numbers of set elements are evaluation criteria are determined. From these two tables, the following slot conditions can be easily retrieved:

1) a∈s3

(frame having S3 including a)

This is apparently noted to be {f1, f5, f7, f9} from a of table Element 1 505.

2) a, b∈s3

(frame having S3 including a, b)

This is apparently noted to be {f5, f7, f9} from the sum of a and b of table Element 1505.

3) s3={a, b}

(frame whose set is {a, b})

From the frame set obtained in 2) above and the OR of the frame set of 2 of table Number 1506, {f5, f7, f9}∩{f2, f8, f9}={f9} is obtained.

4) S3=empty set

From O of table Number 1506, {f3} is obtained.

Figure 16:
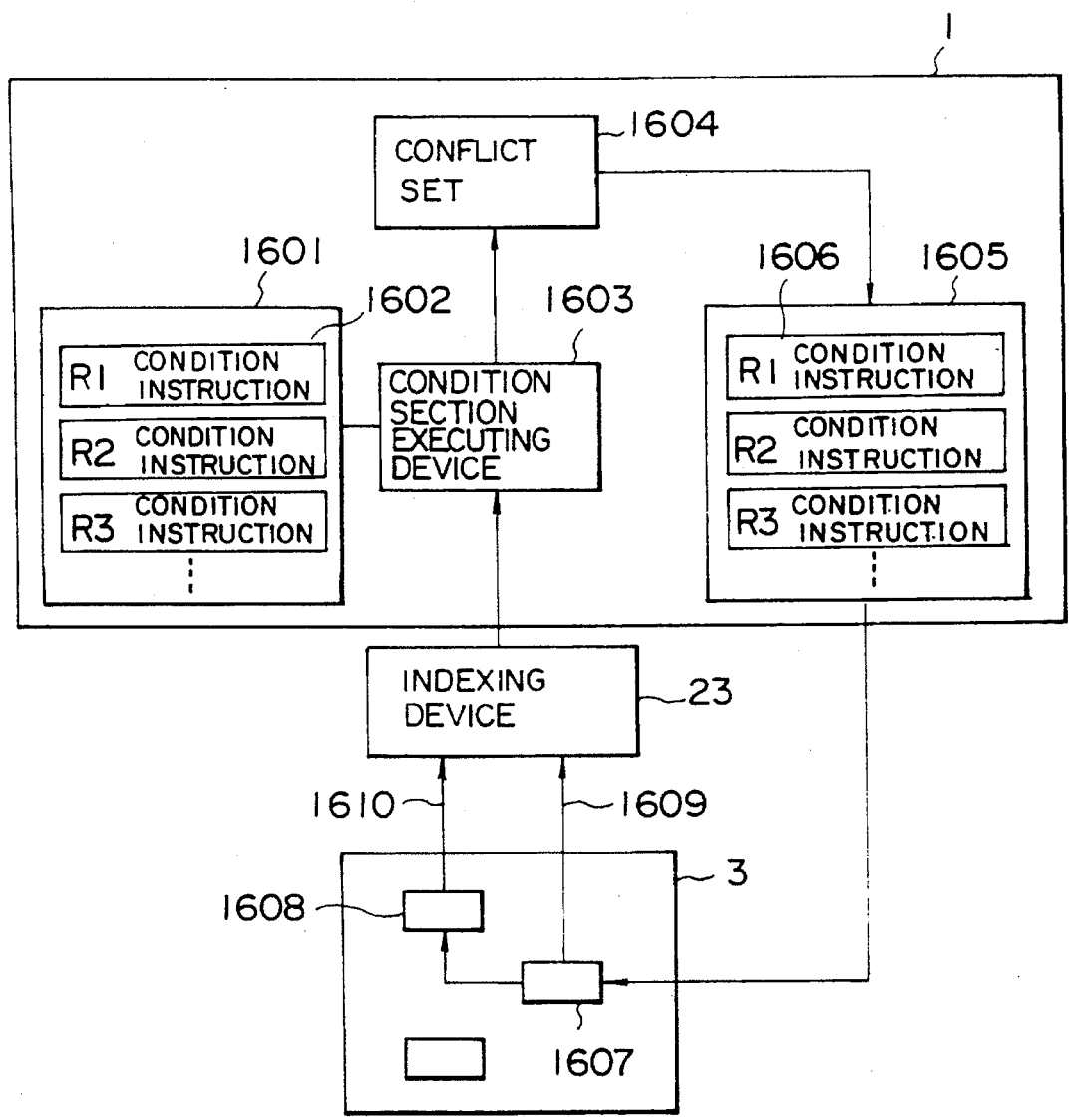
FIG. 16 is a block diagram showing an inference device using the indexing device.

The manner in which the indexing device 23 is used in the condition judgment step of the inference cycle will now be described in connection with FIG. 16. In FIG. 16, 1601 designates a device for storing a condition section of rules stored in the knowledge base. The condition section 1601 of rules is stored as condition instruction rows 1602 and is executed by a condition section executing device 1603. The individual condition instruction row 1602 is an instruction row for executing a condition judgment defined in the condition section of rules. Its algorithm may be described in intermediate language and executed by an interpreter or in compiled machine language. The condition section executing device 1603 executes the condition instruction row stored in the condition section 1601, which condition instruction is referred to by the indexing device 23, and stores the result in the conflict set 1604 of rules and frames.

After selecting an instance to be executed from the conflict set 1604, the inference engine 1 selects an appropriate instruction row 1606 from the instruction section 1605 and executes it. This instruction row 1606, like the condition instruction row 1602, may be intermediate language or compiled machine language. The instruction row 1606 updates the designated slot value for the frame system 3. The frame system 3 performs the updating of a slot value and its associated demon process and method, and transmits the updated information to the indexing device 23. 1607 in the frame system 3 is a frame updated by the instruction row 1606; 1608, a frame in which the slot value is updated by the method from the frame 1607; and 1609 and 1610 represent respective notices to the indexing device 23 of the updated information.

The advantageous results of this embodiment are as follows:

1) since the knowledge expression in the frame system can represent the constitution of knowledge of an object hierarchically, the abstracting of the status needed for the inference process can be defined systematically;

2) since the instance frames corresponding to the actual instruments exist in the lowest layer of frames, no process would be required prior to the input of data from an external source, thus reducing the load of an inference engine;

3) since there exist two kinds of processes, i.e., a foreground process and a background process, the process for maintaining the adjustability of the knowledge base accompanying the change of status of the object system can be separated from the inference process to which the purpose is given, thus simplifying the definition of inference rules;

4) Furthermore, since the adjustment of the inference base was made by the background process upon occurrence of the change of status of the object, the process of recognizing the status of the object has already finished when the inference by the foreground process was started. Namely, the load of the inference engine is reduced so that an inference can be performed by a high-speed foreground process;

5) since the condition judgment is realized by the indexing device without interim memory of the network rule, highspeed judgment can be realized easily even in the large-scale system having many instance frames in the same class. Namely updating of management of frames is realized by updating the slot value tables in the indexing device according to the kind of an updated slot, and updating the slot value tables is easier to perform than reconstituting the interim memories of rule network;

6) in an artificial large system, since the status value to be stored in the slot as slot values of the frames in each layer is limited, the indexing device for retrieving the frame storing the status value in terms of slot values can judge the condition section of the rules connecting plural condition clauses at a high speed.

An expert system according to a second embodiment will now be described in connection with FIGS. 17 and 18. In the first embodiment, the inference device using only the indexing device of the slot values for judgment of condition is described. In the second embodiment, part of the frames adopt the conventional rule network, and the indexing device is used for condition judgment of the remaining frames.

Figure 17:
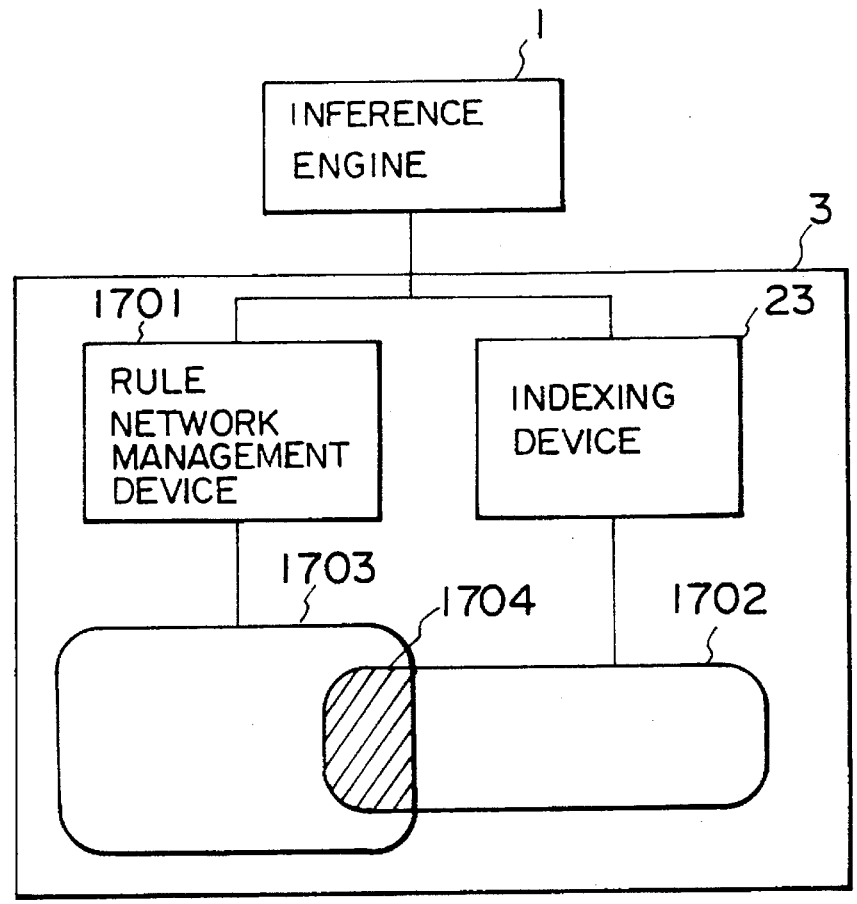
FIG. 17 is a block diagram showing an expert system according to a second embodiment of the present invention.

In FIG. 17, the frame system 3 includes the indexing device 23 and the rule network managing device 1701. Frames set 1702 is under the management of indexing device 23. Frames set 1703 is under the management of the rule network managing device 1701, and frame set 1704 is under the management of both of these two devices 23, 1701.

The rule network managing device 1701 manages the conventional rule network, in which the frames 1703 are stored as the data of interim memory. In this embodiment, all of the ordinal rules are under the management by the rule network managing device 1701, constructing the rule network. The type of frames to be defined in the knowledge base is proper for two types such as the set frames 1702 and the set frames 1703.

The frames 1702 are used chiefly in the inference in the background mode, and the slot values are updated when the status of the object system is changed. The frames 1703 are frames to be referred to from the condition section of the rules in the ordinary rule network.

Figure 18:
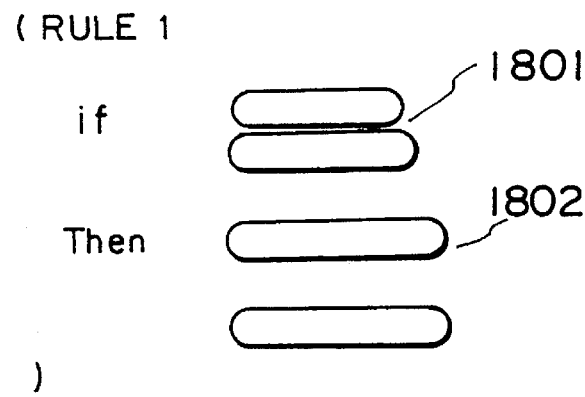
FIG. 18 is a diagram showing the structure of a rule used in the second embodiment.

As shown in FIG. 18, in the condition section 1801 of the rules to be used in this embodiment, there is provided a condition that only frames of the frame sets 1703 can be described. In the instruction section 1802 of the rules, the operation of both frames 1702 and 1703 can be described.

In this case, the retrieval condition to be given to the indexing device is used as the process of execution of the rules. For example, if the process of execution "obtain all frames in which the value of slot X is A, then issue a message to all of these frames" is defined in the rules, an instruction to be given to the indexing device would be to read "obtain all frames in which the value of the slot X is A".

The operation of this embodiment will now be described. If the status of the object system is changed, the slot values of the instance frames representing the constituent elements of the object system are updated by the inference process in the background mode, and then the frames of the upper layer in the frame set 1702 are updated. And, since partial frame set 1704 of frame set 1702 also belongs to frame set 1703, interim memories of rule network under the management of the rule network management device 1701 is updated when the frame of partial frame set 1704 is updated.

When the inference in the foreground mode is started, the inference engine obtains a conflict set by using the rule network of the rule network managing device 1701 for conflict resolution, and executes the selected rule. If there is in the instruction section of the rules an operation of the frame sets 1702, the interim memories of the rule network are updated. If there is an operation of the frame sets 1703, the inference process is performed in the form of a message. If the frames 1704 are updated derivatively by the process to the frames 1703, the interim memories are also updated.

This embodiment has the following advantageous results:

1) since the frames to be updated are relatively few and frames to be referred to from the condition section of many rules are held in the interim memory of the rule network, an inference for the frames having such features can be executed in the foreground mode at a high speed;

2) since the frames updated frequently and suitable for the background mode are managed by the frame system of hierarchical structure, an inference for recognizing the status of an object system can be executed at a high speed; and 3) since the frames to be frequently updated can be canceled from the interim memory of the rule network, a high-speed inference utilizing the merit of the condition judgment algorithm using the rule network can be executed.

Figure 19:
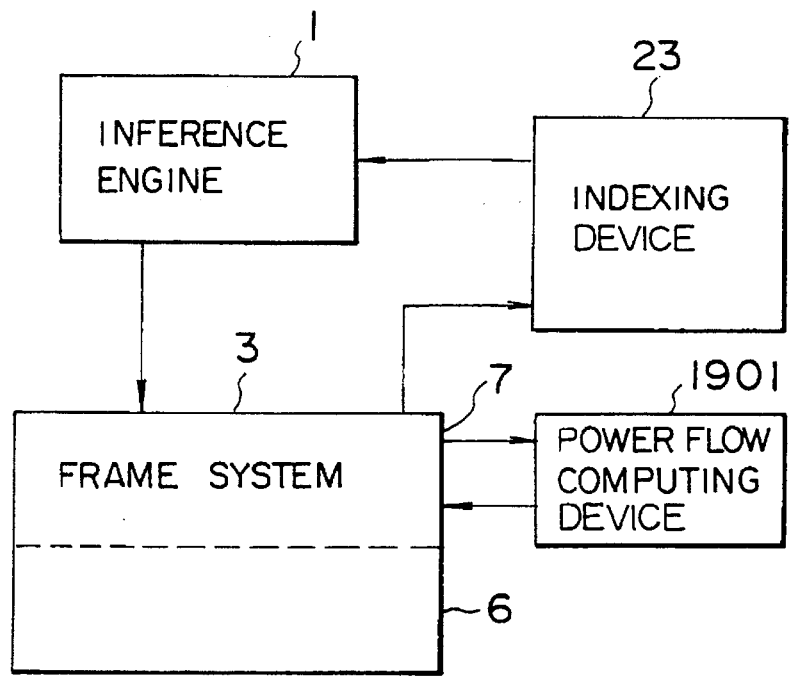
FIG. 19 is a block diagram showing an expert system according to a third embodiment of the present invention.

A third embodiment, in which the expert system is applied to a system for performing a power flow computation, will now be described in connection with FIG. 19. In FIG. 19, reference numeral 1 designates an inference engine; 23, an indexing device; and 1901, a power flow computing device. The basic systematic data 6 of an object electric system is defined in a lower layer in a frame system. Here assume that a power flow computation of the system is designated.

If expressions suitable for the power flow computation are given to systematic data 6 in an upper layer, the power flow computing device 1901 performs a process based on this systematic data and returns the result. If the systematic data 7 are not yet defined, or if the status of the basic systematic data 6 are changed, the systematic data 7 of an upper layer must be redefined.

The constitution of FIG. 19 is capable of giving to the frame system 3 the systematic data of the expressions, which can be processed by the power flow computing device 1901, by the inference engine 1 and the indexing device 23.

Figure 20:
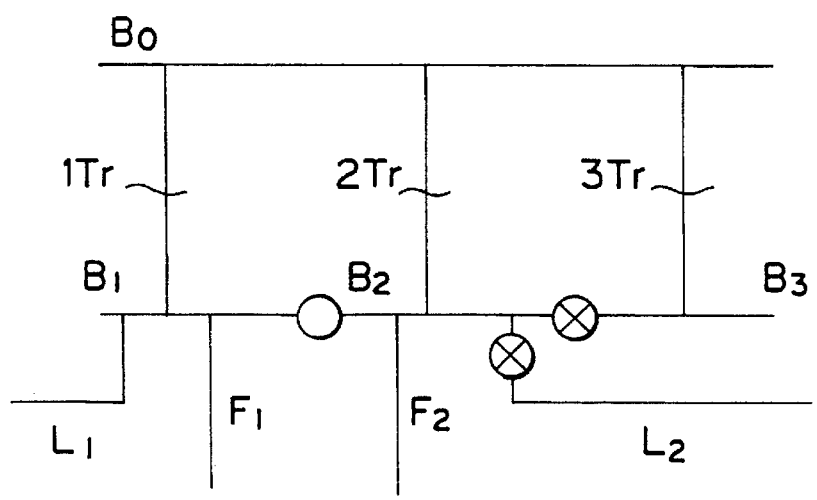
FIG. 20 is a skeleton diagram of a system for which a power flow computing process is to be performed.

FIG. 20 is a skeleton diagram showing an object electrical system for which a power flow computing process is to be performed. FIG. 21 shows frame expressions of instruments constituting the object system of FIG. 20. Now the systematic data needed in a power flow computation is previously simplified than that given from FIG. 20.

In the system, buses B1 and B2 and a power transmission line L1, which are electrically connected, all belonging to the same voltage class, must be expressed virtually as a single node in view of electric circuit computation.

Further, since two transformers 1Tr and 2Tr are adapted for parallel operation, 1Tr and 2Tr must be expressed virtually as a single transformer. Such operation for virtually putting a plurality of instruments together is called "grouping".

Figures 22, 23:
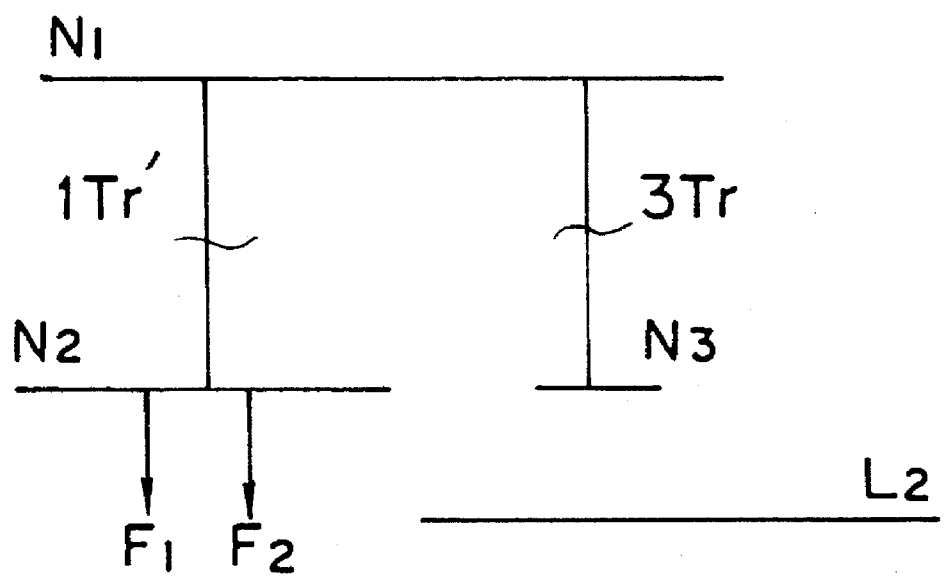
FIG. 22 is a diagram showing the system after a grouping process of the power flow computing process.
FIG. 23 shows a rule for finding out the bus to be subjected to the grouping process.

FIG. 22 shows the system of FIG. 20 after having been grouped into such an expression which can use the power flow computing device 1901. FIG. 23 shows a rule for locating the bus to be a criterion of the grouping.

The bus that satisfies the condition on the kind of the instruments of a first condition 2301 is obtained by the indexing device 23. A second condition is obtained by a complement of the set that the slot 'connection' is not empty, namely, the complementary set of the set of 'number of elements is 0'.

If this rule is used in the system of FIG. 20, the first condition is {B0, B1, B2, B3}, and the second condition is {B1, B2, C1}, and the frame that satisfies the rule of FIG. 23 will be {B1, B2} from the logical AND of these two conditions. As the frames of the same voltage are traced with the thus obtained frames as criteria, the grouping of the bus will terminate.

After grouping, a node name is set to a slot 'node' as a flag for the frames of the instruments associated with the same node. The bus which is not to be an object of grouping can be thought as a single node by itself.

Figure 24:
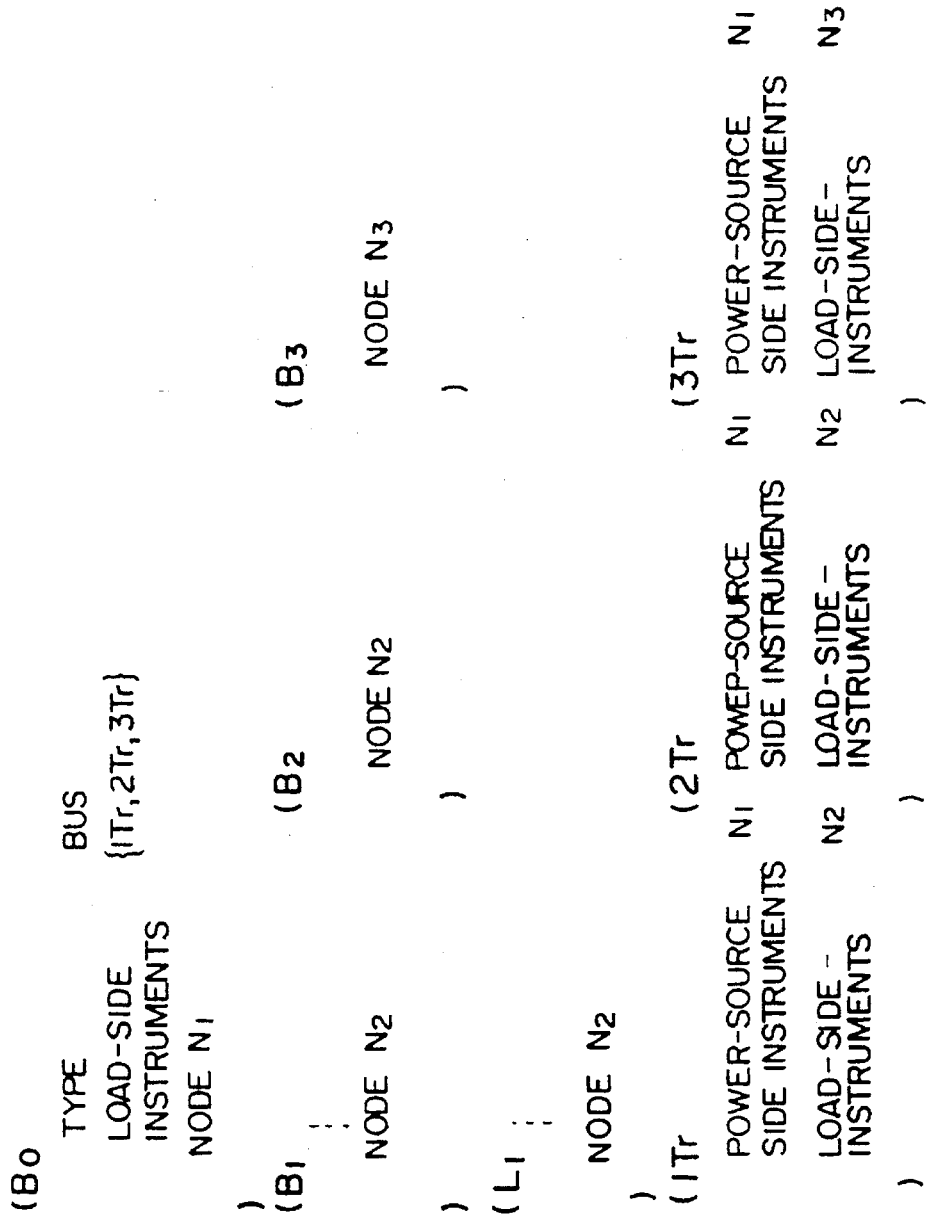
FIG. 24 shows frames after the grouping process.

FIG. 24 shows the frames after the slot 'node' have been set. The slot 'power-source-side instruments 'and the 'load-side instruments' of transformers are changed in node name.

The grouping of parallel transformers, as the step next to the grouping, will now be described. Since the transformers 1Tr and 2Tr are connected to the same node after grouping, they must be summarized. If attention is paid to the transformer 1Tr, 2Tr is an object of summarizing, and 3Tr is not an object.

Figures 25, 26:
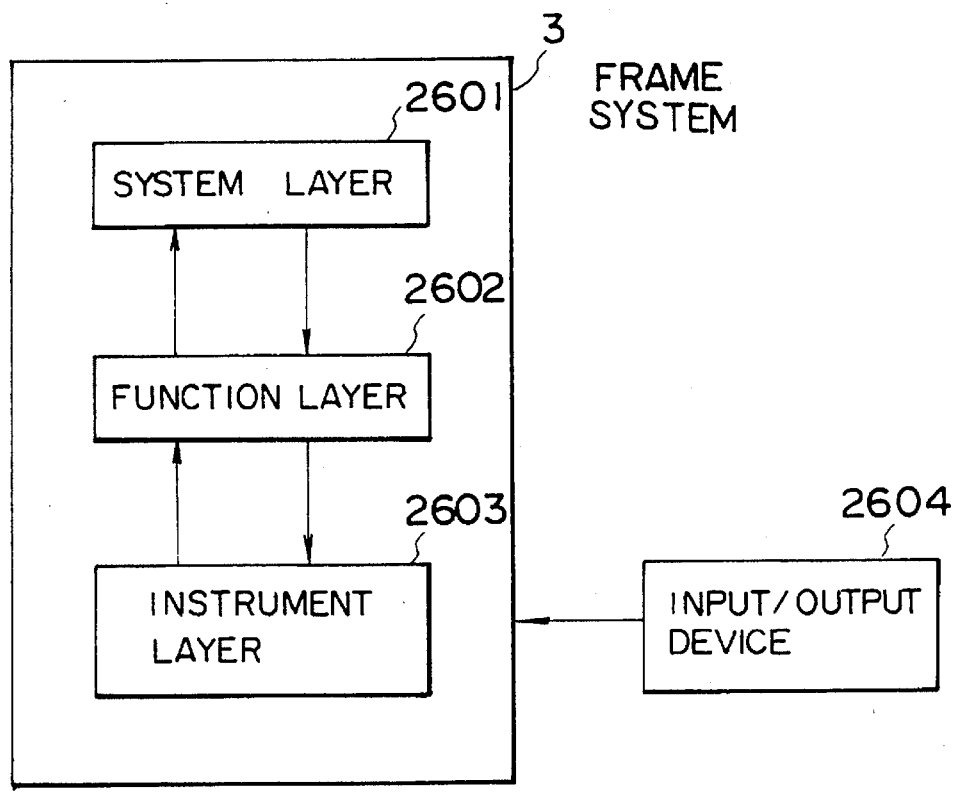
FIG. 25 shows rules for locating a transformer which can be summarized.
FIG. 26 is a block diagram showing an expert system according to a fourth embodiment of the present invention.

FIG. 25 shows rules for retrieving summarizable parallel transformers. If the transformer 1Tr is an object, the power source-side instruments and the load-side instruments are obtained from the slot values, and the parallel transformers are determined, based on these values, from the second condition by the indexing device. Therefore, it is possible to put the parallel transformers together. From the foregoing processes, the constitution of systematic data 7 expressions requiring the power flow computing device is completed.

The third embodiment has the following advantageous results. If there is no indexing device, the retrieval of the frames is increased, such as when matching them with the rule of FIG. 23, with the increase of the number of frames. Since the number of frames constituting data of an electric power system as a practical object to be controlled is several hundreds to several thousands, on-line control in real time is difficult to achieve.

Since the coefficient of retrieving the frames is not influenced by the number of frames, this embodiment equipped with the indexing device is suitable for both the control of electric power system and the control of large-scale data system.

A fourth embodiment, in which service interruption of the system is judged by the inference using information propagation between layers of the expert system, will now be described. 3 in FIG. 26 designates a frame system having a plurality of layers. The frame system 3 represents the electric power system. 2601 designates a layer representing the system by a substation and information of power transmission; 2602, a layer representing the system by a function of the instrument and interconnection; and 2603, a layer representing the system by instruments. 2604 designates an input/output device for accessing the content of the frame system.

If the status of an instrument of the object system is updated, the status of instrument of the layer 2603 is updated by the input/output device 2604 so that information propagation between layers is initiated to perform an inference.

Figure 27:
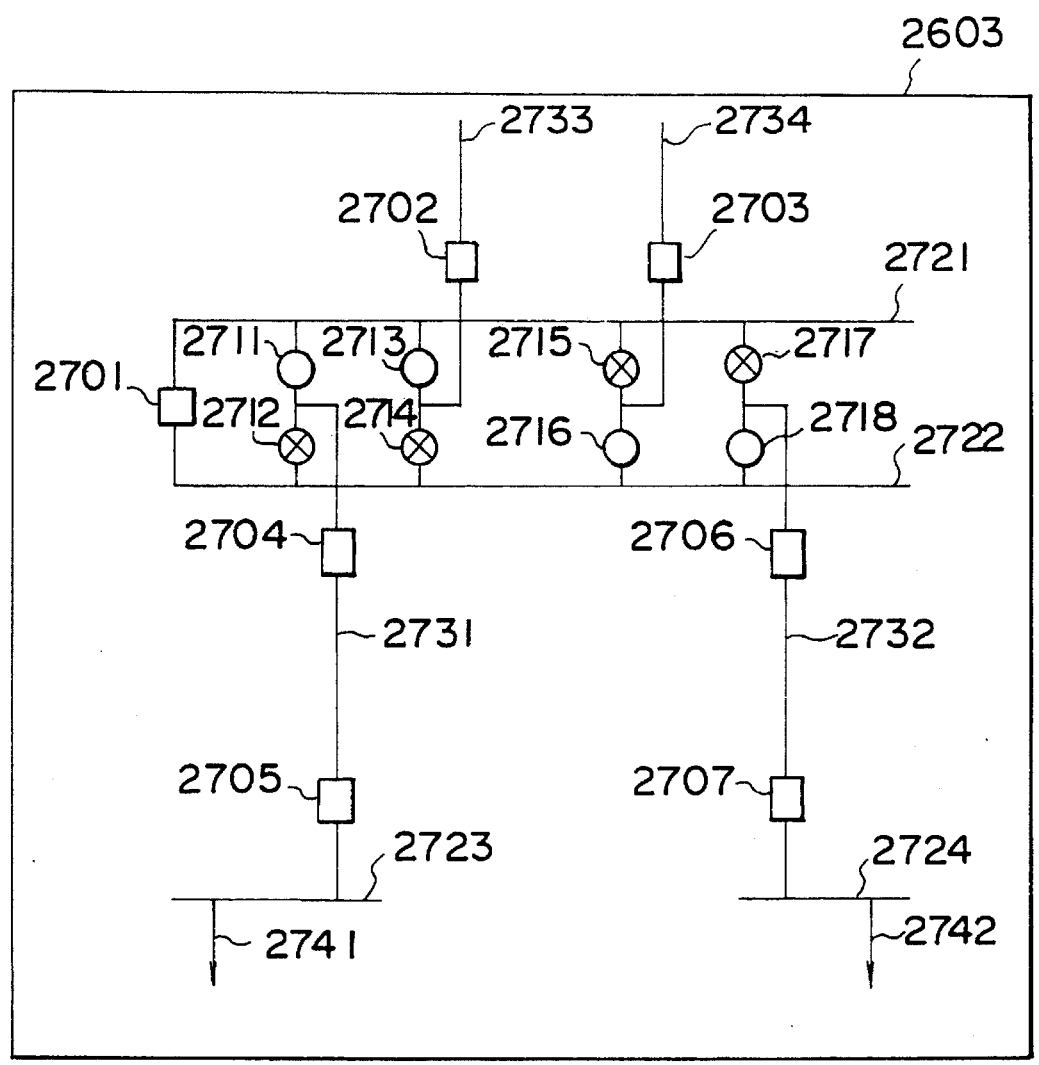
FIG. 27 is a diagram showing a detailed layer in which various instruments are defined in instrument levels.

The inference for grasping the status of service interruption due to an accident in the system will now be described. FIG. 27 is a detailed diagram showing a layer 2603 in which the instruments and the like are defined in instrument level.

In FIG. 27, 2711, 2713, 2716 and 2718 designate switches in closed status; and 2712, 2714, 2715 and 2717, switches in open status. When the status of instruments are updated by an accident of the bus 2722, CB (breaker) 2703, CB 2701 and CB 2706 are changed into a trip status. The trip status is a status in which the breakers are opened by an instruction from a relay.

Information of voltage concerning a power transmission line 2732 is changed to zero. This change of information is transmitted to an upper layer 2602.

Figure 28:
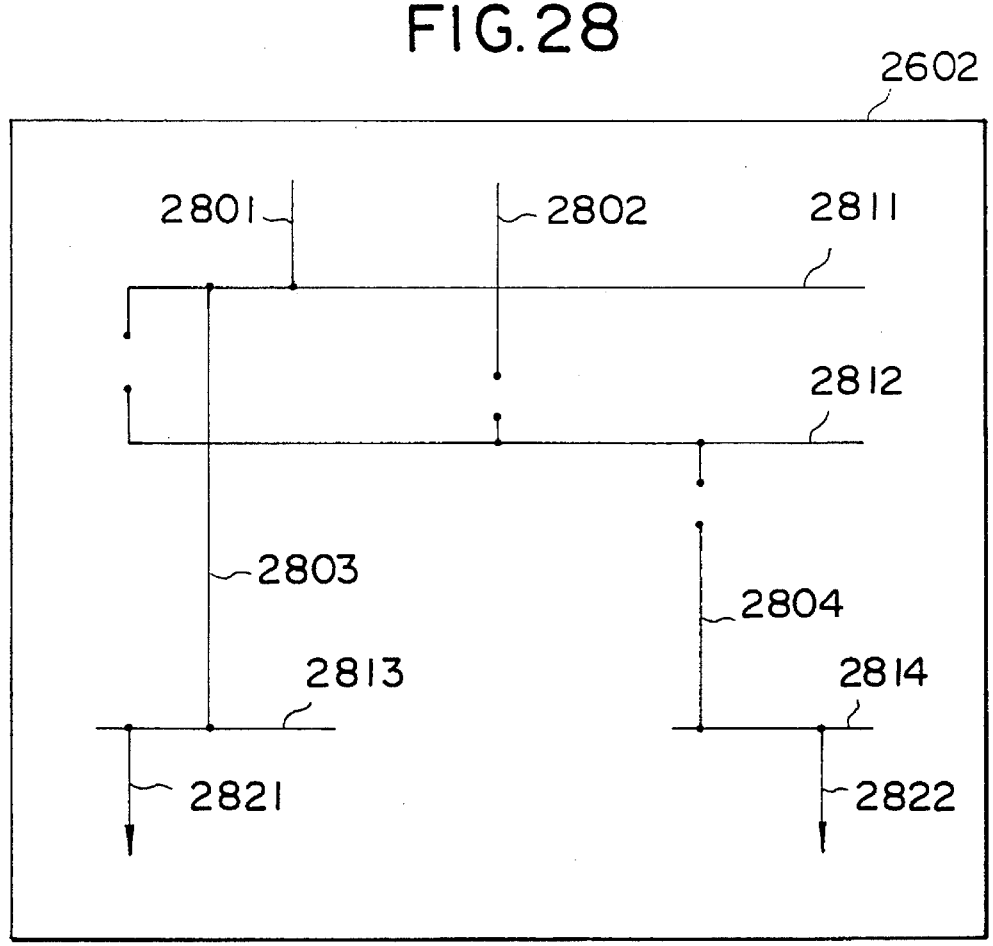
FIG. 28 is a diagram showing a detailed layer in which various instruments are represented in terms of functions and interconnections.

FIG. 28 is a detailed diagram of the upper layer 2602. When a notice that the status of CB 2703 was changed to a trip status is given, the connection of a power-transmission line 2802 and a bus 2812 is changed to OFF status. Similarly, the trip information of CB 2701 changes the connection between a bus 2811 and a bus 2912 to OFF status and the trip information of CB 2706 changes the connection between bus 2812 and a power-transmission line 2804 respectively to OFF status.

The voltage information of the power transmission line 2732 is transmitted to the power transmission-line definition 2804 of the upper layer 2602, and the information in the power transmission-line definition 2804 is also updated to 'absence of voltage'. The status changes in these layers is transmitted to a further upper layer 2601.

Figure 29:
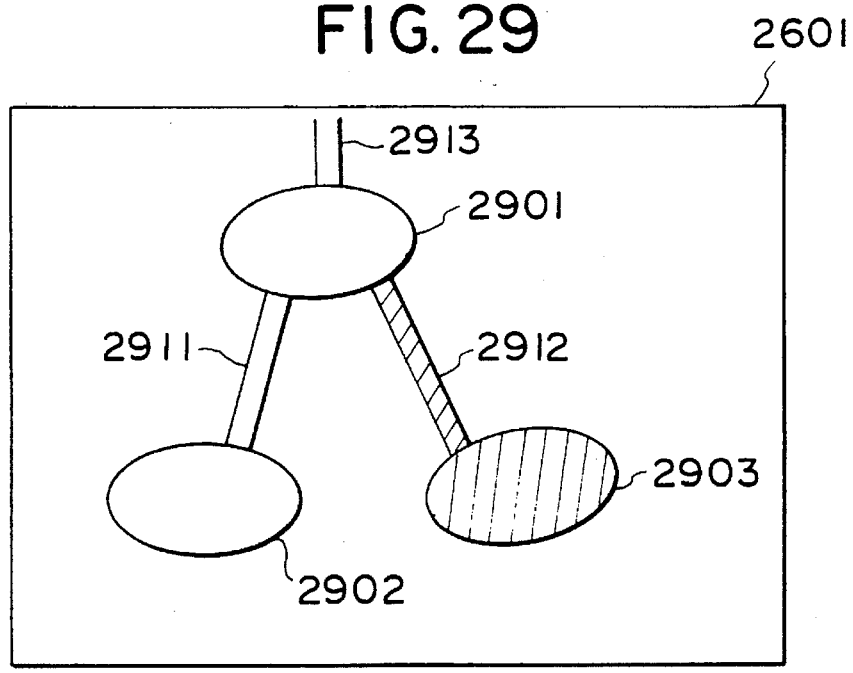
FIG. 29 is a diagram showing a detailed layer of transformer level.

FIG. 29 is a detailed diagram showing the uppermost layer 2601 called substation level layer. The information in the layer 2601 is also updated by the updating of status in the layer 2602. The change of connection regarding the bus 2812 in the layer 2602 is transmitted to a substation 2901 to set the information of change of status in the substation 2901 in the layer 2601. The voltage information from the power transmission line 2804 is transmitted to a power transmission line 2912.

The power transmission line 2912 is thereby changed to a status "disable to supply electric power". From the foregoing information, the substation 2901 in which the information of change of status is set is estimated as a cause for accident.

Furthermore, since the power-transmission line 2912 is in a status disable to supply electric power, it can immediately be concluded that a substation 2903 is totally stopped. Partly since there are no information of change of status in the power-transmission line 2911 and a substation 2902, and partly since electric power supply is normal, it can be concluded that a normal status is maintained. Therefore, it is not necessary to judge substation 2912 whether there is stoppage of electric power supply or not, and it is noted that only the substation 2901 needs to be examined in order to grasp a detailed system status.

Then, the following instructions are issued from the layer 2601 to the layer 2602. One instruction is the instruction "make a detailed determination" of the statuses of the instruments of the layer 2602 under the substation 2901. Another instruction is the instruction "all of the instruments under the substation 2903 are not receiving electric power supply".

According to this instruction, 'voltage' is judged from the status of connection regarding the bus 2811 and the bus 2812 in the layer 2602, and bus 2811 is judged as "powered" because an electric power supply is received. The bus 2812 is judged as 'not receiving electric power supply' because there is no power supply from anywhere. The bus 2814 and the load 2822 associated with the substation 2903 is immediately judged as 'not receiving electric power supply'.

Furthermore, the foregoing information is transmitted from the layer 2602 to the instrument level layer 2601 so that the voltage status of every instrument is determined. The fourth embodiment has the following advantageous results:

(1) since information in the object system is automatically summarized or abstracted by information propagation between layers, even a huge amount of data of an object electric power system can be processed with improved efficiency;

(2) the second advantageous result is to improve the modularity of data; all data of the respective layers can be processed according to the information contained by the respective data themselves, therefore it is easy to amend and expand system data;

(3) the third advantageous result is that the constitution of the system can be easily understood; the data expression of every layer and propagation of instructions are similar to grasping the system of a human and hence can easily be understood very intuitively;

(4) the fourth advantageous result is that the system has a parallel structure; assuming that the system is to be realized by a computer, since each layer and operation of data units are highly independent, it is easy to make them with computer processors, and therefore because of the parallel processes, a high degree of processability can be achieved.

A fifth embodiment will now be described in which the expert system of this invention is applied to an interactive system of planning the operation plan of instruments of an electric power system. In FIG. 30, 3000 designates a computer used in this embodiment; and 3001, a display.

3002 designates a controller for controlling the entire computer 3000; 3003, an interface managing device for managing the input/output of information with a human; 3004, an inference engine; 3005, a frame system; 3006, an interface managing device for performing the input/output of information with an object electric power system; and 3007, an analysis program library in which various numerical calculation programs to be used by the controller 3002 or the inference engine 3004 are stored.

In the frame system 3005, there are frames constructed hierarchically concerning the structure of the object electric power system. 3008 designates a layer representing the system constitution; 3009, a layer representing the connection of buses in the substation and power station; and 3010, a layer representing the constitution of the individual instrument.

Figure 31:
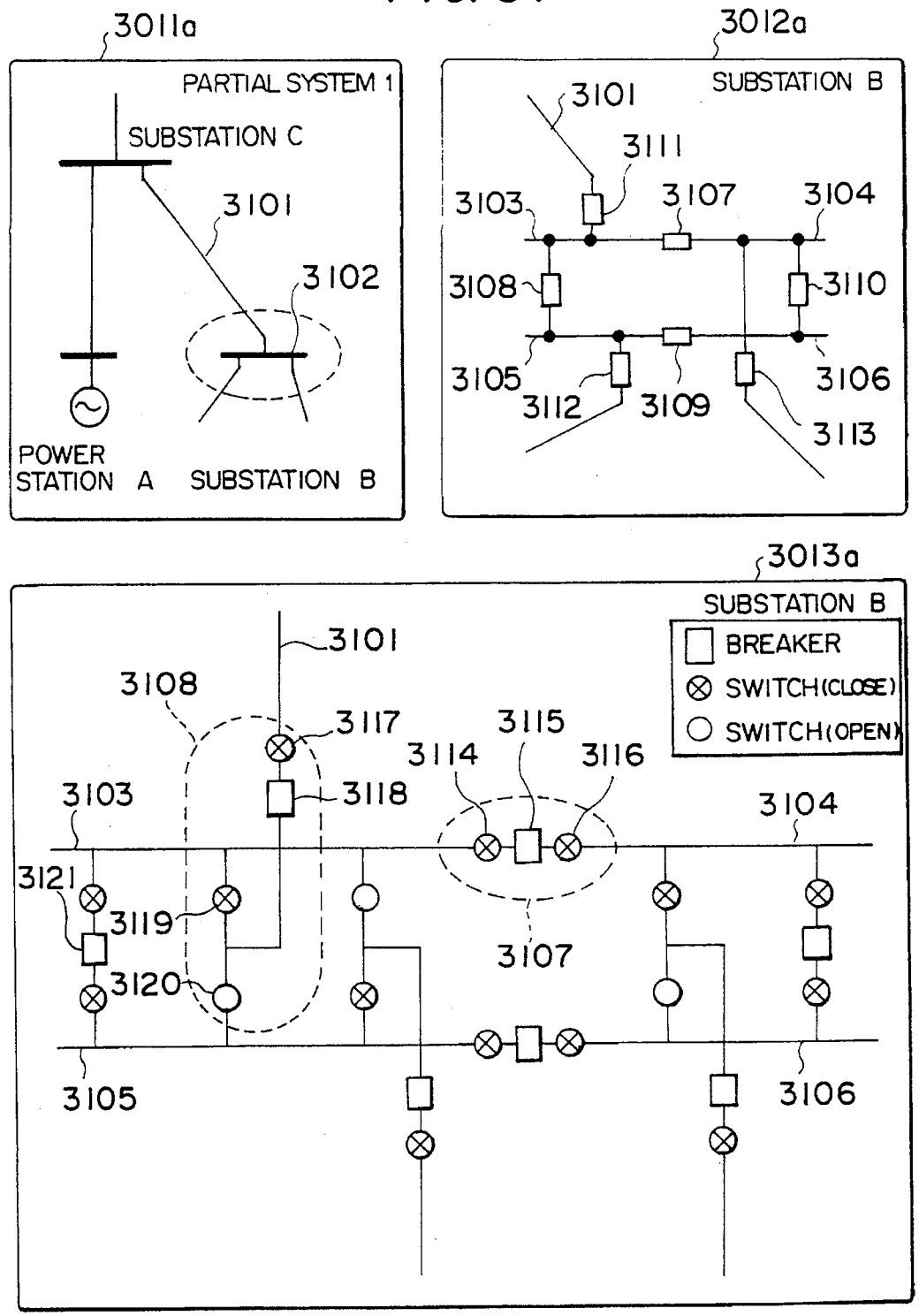
FIGS. 31 and 32 are diagrams showing typical display screens representing an electric power system.

Furthermore, the status of these layers are represented as indicated by 3011a, 3012a and 3013a as multiple windows on the display 3001. FIG. 31 shows typical display screens 3011a-3013a. In the window 3011a, the power station A and substations B, C are represented as a partial system. 3101 designates a power transmission line connecting the substations B and C with one another; and 3012, representing buses i the substation C.

In the window 3012a, the state of wiring 3102 of the actual bus in the substation C is represented, and buses 3103–3106 are connected to one another via switches 3108–3110. Since all of the switches 3108–3110 are closed, the buses 3103–3106 can be treated as a single bus (node) in calculation of electric circuit, as indicated by the bus 3102 in the window 3011a. Switches 3111–3113 connect the respective power-transmission lines with the corresponding buses.

3013a designates a lowermost layer display window in which the status of the practical instruments and the connection therewith are displayed. The switch 3107 of the window 3012a is represented by a switch 3114, a breaker 3115 and a switch 3116 in the window 3013a.

Furthermore, the switch 3111 is composed of a switch 3117, a breaker 3118, a switch 3119 and a switch 3120 in the window 3013a. In actuality, the switch 3111 is connected to the buses 3103 and 3015 via the switches 3119, 3120, respectively. Depending on the status of the switches 3119, 3120, the power transmission line 3101 may be displayed in the window 3012a as being connected to the bus 3103 in some occasions and being connected to the bus 3105 in other occasions.

Such connections of the power-transmission lines depend on the status of switches in the lowermost instrument layer 3010 in the frame. Therefore, if the status of a switch is changed in the instrument layer 3010, this change must be reflected on the status of an upper layer.

Figure 32:
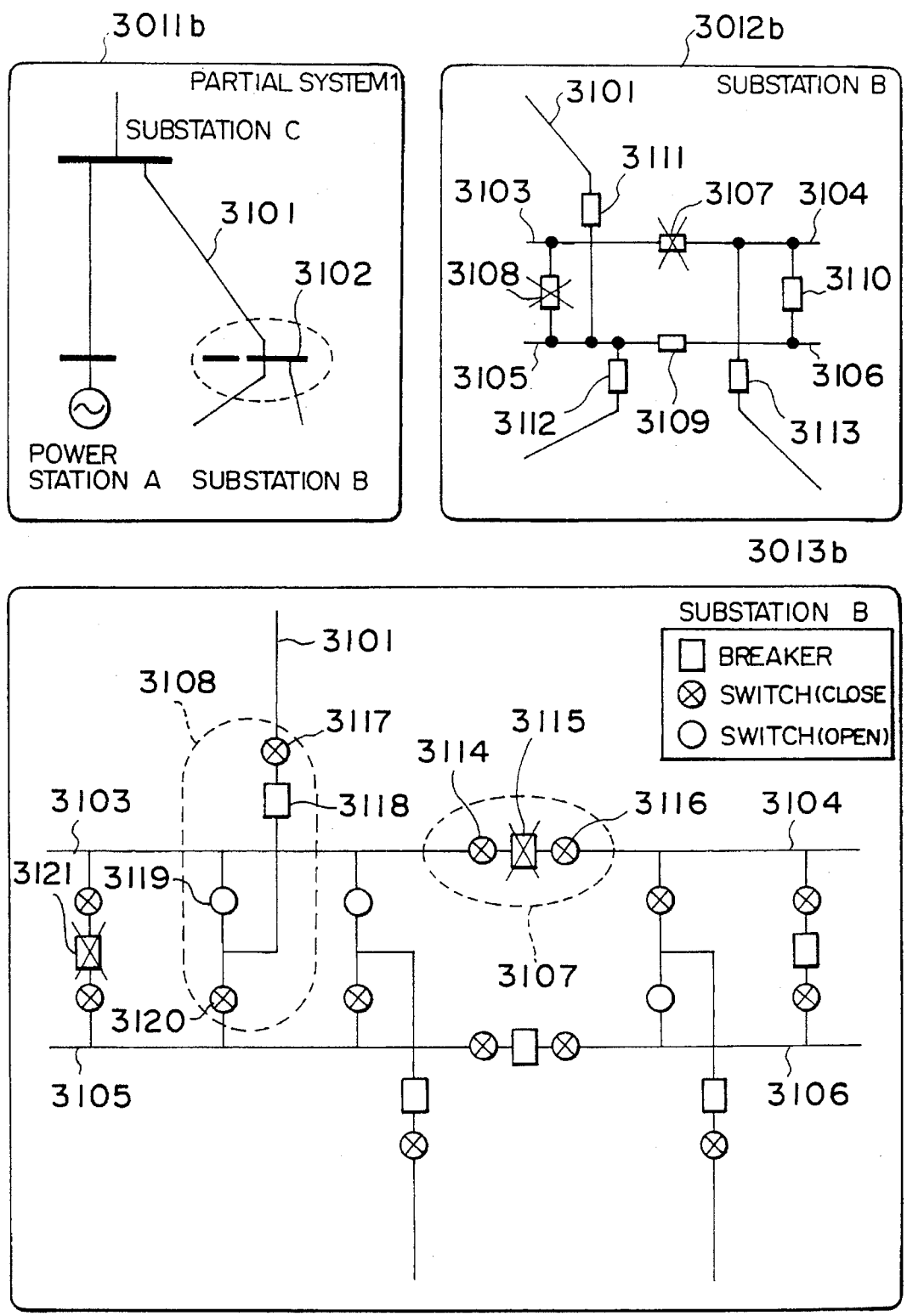

For example, as shown in FIG. 32, when the breakers 3121, 3115 become open, the switch 3119 is changed from the closed status to the open status, and the switch 3120 is changed from the open status to the closed status, the display showing the status of respective instruments is immediately changed as displayed in the window 3011b of FIG. 32. As displayed in the window 3012b showing the connection layer 3009, the bus to which the power-transmission line 3101 is connected must be changed from 3103 to 3105, and the display of the switches 3107, 3109 also must be changed from the closed status to the open status. In the window 3011b shown in the system diagram, a display that the bus is separated into two.

The expression of knowledge in the fifth embodiment for providing the above-mentioned functions, and the content of operation will now be described in connection with FIG. 33. In this embodiment, a graphic showing the instrument displayed on the display screen corresponds to a frame.

Figure 33:
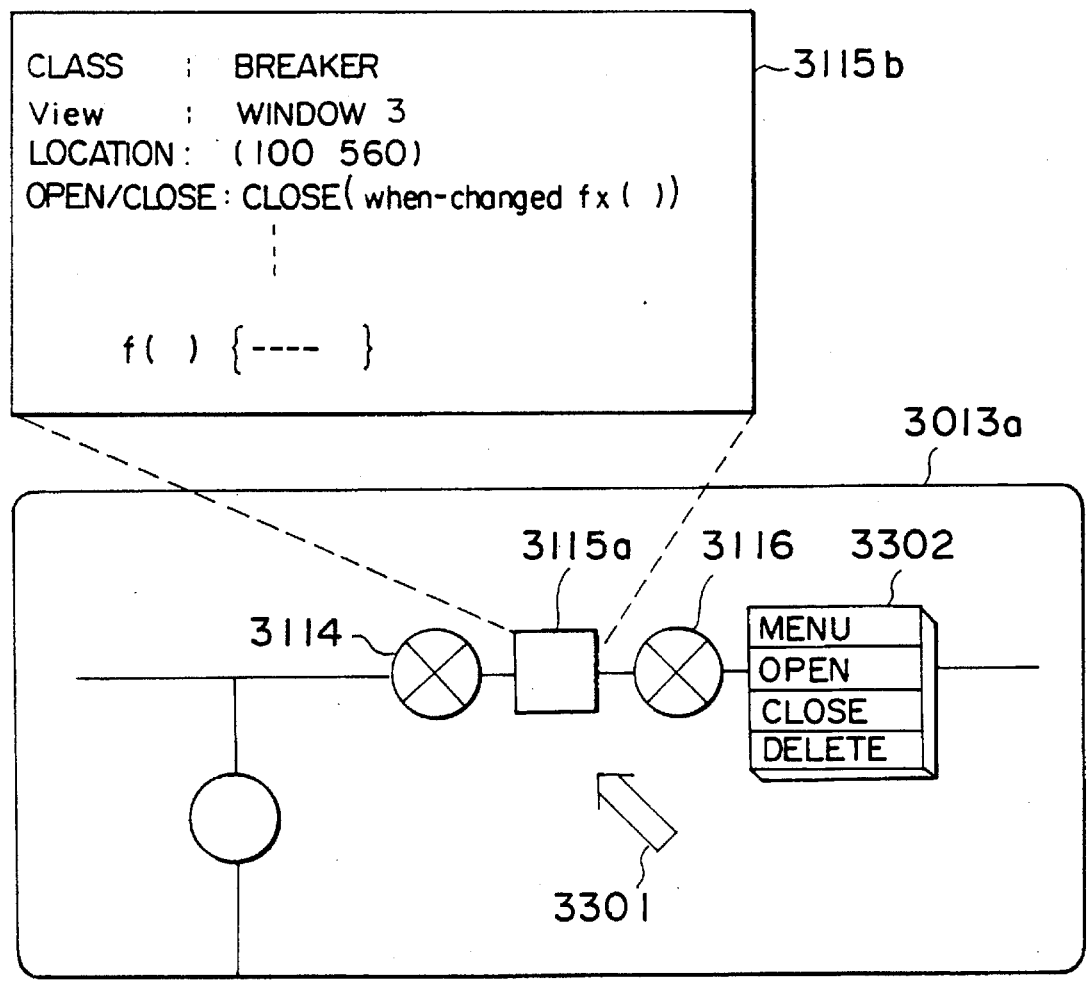
FIG. 33 is a diagram showing graphics on the screen and the coordinate relation of a frame.

In FIG. 33, 3013a designates a window in which an instrument layer 3010 is to be displayed; and 3115b, a frame corresponding to the breaker 3115a. In the frame 3115b, there are defined, as slots, 'View' representing the window to be displayed, 'location' representing the position in the window where breaker 3115a to be display, 'open/close' representing the status of open or closed, etc.

3301 designates a cursor of a mouse in 3013a. The operation of an instrument displayed in 3013a is started by selecting an object instrument by this cursor, and by selecting a function menu of a pop-up menu 3302.

For example, if 'open' in the menu 3302 is selected, a message instructing that the open/close status is the open status is transmitted to the frame 3115b. By this message, the slot value of the slot 'open/close' is updated to 'open'. In this slot, a demon fx0 is determined with an attribute 'when-changed', and fx0 changes the display of the window 3115a to be displayed in 3013a, depending on the 'open/close' status.

Figure 34:
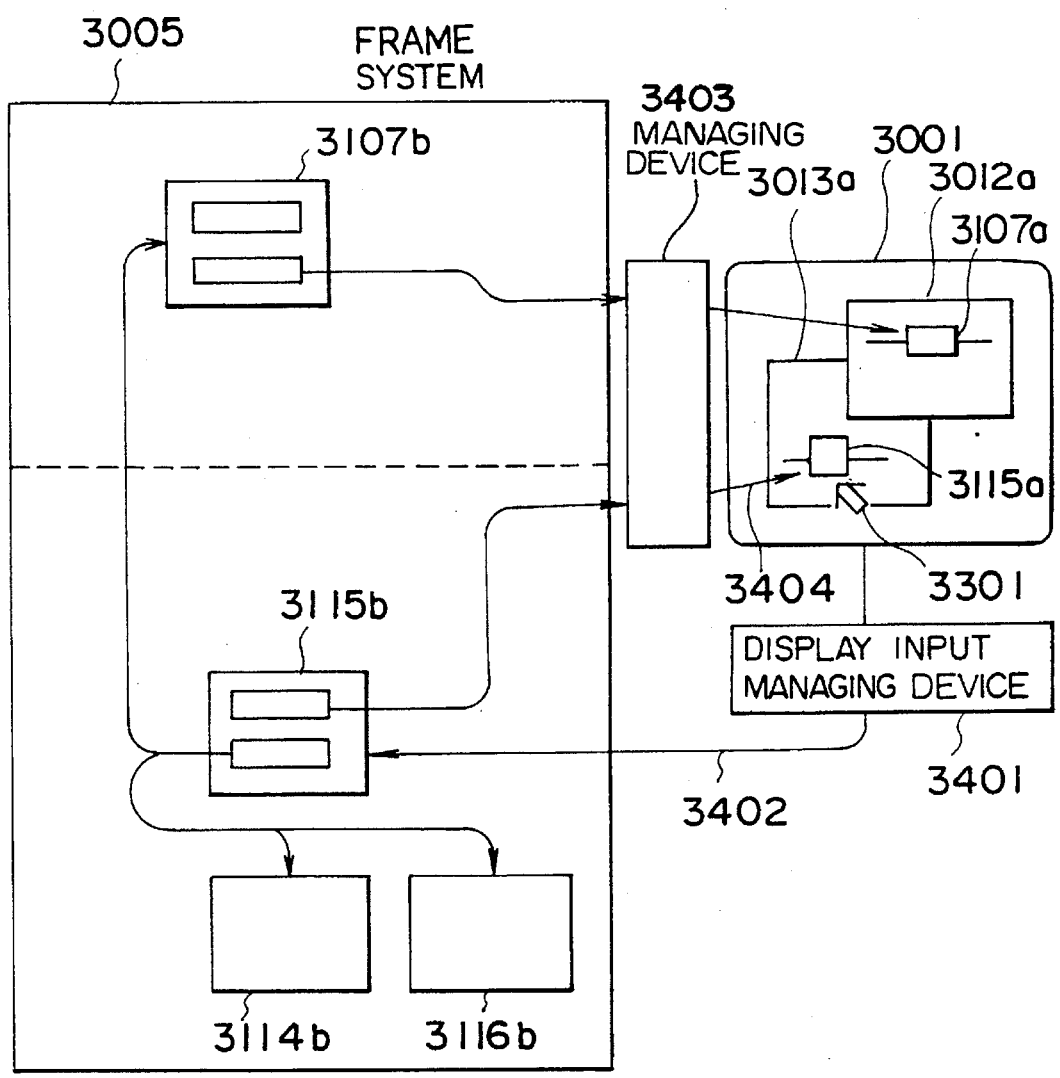
FIG. 34 shows the manner in which the expert system of the fifth embodiment of the present invention operates.

FIG. 34 shows the operation of this system. In FIG. 34, 3012a designates a connection layer window; 3107a, a connection layer switch; 3013a, an instrumental layer window; and 3115, a breaker. 3401 designates a display input managing device for managing a cursor 3301 of a mouse, discriminating both an object selected by cursor 3301 and the menu selected by cursor 3301 to determine a message to be executed, and issuing the message to the object.

As discussed above in connection with FIG. 33, when the breaker 3115a is selected by the mouse to instruct the switch to open, a message 3402 for instructing the switch to open is sent to a frame 3115b. After the frame 3115b which received the message has performed the operation which is defined by the message, a request to change the display of the graphics 3115a from 'closed' to 'open' is given to an output managing device 3403 of the display 3001 so that the redrawing 3404 of the graphics is executed.

Further, the frame 3115b sends to associated frames 3114b, 3116b, 3107b a message that the open/closed status in the frame 3115b has been changed. 3107b designates a frame of the connection layer 3009 representing a switch abstracted from the instrument layers 3114b, 3115b, 3116b. In the frame 3107b, both information concerning instrument 3114b, 3115b, 3116b which belong to 3107b and a method in which the switch 3107b will be 'open' as any of the instrument 3114b, 3115b, 3116b becomes 'open' are defined, so that the switch 3107b will be 'open' and give to the output managing device 3403 a message that the status of display of the graphics 3107a is to be changed from 'closed' to 'open'.

As described above, in this embodiment, when the status of the individual instrument is changed, the status of the abstracted upper layer is automatically updated, and the display is also changed.

The fifth embodiment has the following advantageous results:

according to levels of various view points which a human has for the system, knowledge expressions from the expression of a general system to the expression of an individual instrument can be hierarchically displayed on the display;

the frames representing both the individual instruments in the frame system and the abstracted instrument units are respectively corresponding to the graphics to be displayed on the display screen; partly since the status of the individual frame can quickly be displayed on the screen, and partly since data change can be performed visually on the display screen, designation can be made with few mistakes;

since the status of the abstracted frame to which the instrument belongs is updated when the status of the individual instrument is changed, the adjustability between specific data and its abstracted data is automatically maintained so that the maintenance of adjustability of the frame system can be realized; and since the graphic element corresponding to each status of the individual frame is built in each frame as a demon, being independent of the other graphic elements, it is possible to simplify the graphics managing so that the changing and correcting of the function is facilitated.

As discussed above, according to this invention, it is possible to provide an expert system which enables a high-speed inference even in a large-scale system.

What is claimed is:

1. An expert system for processing knowledge of an object system that has a plurality of elements, comprising:
 a) a knowledge base including a plurality of knowledge elements each of which is a framework for representing knowledge, and comprising a plurality of logical layers including:
  (i) a unit knowledge element descriptive layer comprising a portion of said plurality of knowledge elements each of which contains knowledge for representing a portion of a first model of the object system, said portion of the first model of the object system corresponding to each one of the plurality of elements of the object system, respectively; and
  (ii) a summarized knowledge element descriptive layer being hierarchically arranged above said unit knowledge element descriptive layer, and comprising a second portion of said plurality of knowledge elements each of which contains knowledge for representing a portion of a second more abstract model of the object system than said first model, said knowledge elements of said second portion corresponding to knowledge of at least one of the knowledge elements of said first portion; and
 b) a processor for generating knowledge from the knowledge including updated knowledge contained in the knowledge elements included in the unit knowledge element descriptive layer, to represent the second model of the object system, and storing the generated knowledge in the knowledge element included in the summarized knowledge element descriptive layer, said knowledge element in which the generated knowledge is to be stored corresponding to the knowledge element containing the updated knowledge, said updating being based on a change of status in the object system or on an explicit instruction;

wherein each of said knowledge elements is a frame and each of said knowledge elements included in the unit knowledge element descriptive layer is a frame having a slot storing an output value of a sensor that observes a status value of the respective elements in the object system, and said processor performs said generating and storing in response to updating of a slot value of a frame included in the unit knowledge element descriptive layer according to a Demon process described in association with the updated slot.

2. An expert system for processing knowledge of an object system that has a plurality of elements, comprising:

a) a knowledge base including a plurality of knowledge elements each of which is a framework for representing knowledge, and comprising a plurality of logical layers including:

(i) a unit knowledge element descriptive layer comprising a portion of said plurality of knowledge elements each of which contains knowledge for representing a portion of a first model of the object system, said portion of the first model of the object system corresponding to each one of the plurality of elements of the object system, respectively; and (ii) a summarized knowledge element descriptive layer being hierarchically arranged above said unit knowledge element descriptive layer, and comprising a second portion of said plurality of knowledge elements each of which contains knowledge for representing a portion of a second more abstract model of the object system than said first model, said knowledge elements of said second portion corresponding to knowledge of at least one of the knowledge elements of said first portion; and b) a processor for generating knowledge from the knowledge including updated knowledge contained in the knowledge elements included in the unit knowledge element descriptive layer, to represent the second model of the object system, and storing the generated knowledge in the knowledge element included in the summarized knowledge element descriptive layer, said knowledge element in which the generated knowledge is to be stored corresponding to the knowledge element containing the updated knowledge, said updating being based on a change of status in the object system or on an explicit instruction;

wherein said object system is an electric power system, and said processor performs said generating and storing in response to updating of knowledge of a knowledge element included in the unit knowledge element descriptive layer.

* * * * *

UNITED STATES PATENT AND TRADEMARK OFFICE
CERTIFICATE OF CORRECTION

PATENT NO. : 5,506,938
DATED : 9 April 1996
INVENTOR(S) : Chihiro FUKUI et al.

It is certified that error appears in the above-identified patent and that said Letters Patent is hereby corrected as shown below:

| Column | Line | |
|---|---|---|
| 9  | 12 | After "external" insert --event--. |
| 10 | 11 | After "increased" delete "the". |
| 11 | 44 | Change "that" to --in which--. |
| 11 | 45 | Change "that" to --in which--. |
| 11 | 60 | Change "S1={f6}" to --S1=5:{f6}--. |
| 11 | 61 | Change "S1={f7}" to --S1=8:{f7}--. |
| 12 | 64 | Change "1) a∈s3" to --1) a ∈ s3--. |
| 13 | 1  | Change "2) a, b∈s3" to --2) a, b ∈ s3--. |
| 16 | 8  | Change "have" to --has--. |

UNITED STATES PATENT AND TRADEMARK OFFICE
CERTIFICATE OF CORRECTION

PATENT NO. : 5,506,938
DATED : 9 April 1996
INVENTOR(S) : Chihiro FUKUI et al.

It is certified that error appears in the above-identified patent and that said Letters Patent is hereby corrected as shown below:

| Column | Line | |
|---|---|---|
| 17 | 33 | Change "are" to --is--. |
| 18 | 42 | Change "i" to --in--. |
| 19 | 15 | Change "a display" to --it is indicated--. |

Signed and Sealed this

Twenty-fourth Day of September, 1996

Attest:

BRUCE LEHMAN

*Attesting Officer*     *Commissioner of Patents and Trademarks*